(12) United States Patent
Kahook

(10) Patent No.: US 10,993,834 B2
(45) Date of Patent: May 4, 2021

(54) LACRIMAL SYSTEM DRUG DELIVERY DEVICE

(71) Applicant: THE REGENTS OF THE UNIVERSITY OF COLORADO, A BODY CORPORATE, Denver, CO (US)

(72) Inventor: Malik Kahook, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 463 days.

(21) Appl. No.: 14/760,307

(22) PCT Filed: Jan. 14, 2014

(86) PCT No.: PCT/US2014/011477
§ 371 (c)(1),
(2) Date: Jul. 10, 2015

(87) PCT Pub. No.: WO2014/113384
PCT Pub. Date: Jul. 24, 2014

(65) Prior Publication Data
US 2015/0351961 A1      Dec. 10, 2015

Related U.S. Application Data

(60) Provisional application No. 61/752,742, filed on Jan. 15, 2013.

(51) Int. Cl.
*A61F 9/00* (2006.01)
*A61F 9/007* (2006.01)
(Continued)

(52) U.S. Cl.
CPC .......... *A61F 9/0026* (2013.01); *A61F 9/0017* (2013.01); *A61F 9/00772* (2013.01);
(Continued)

(58) Field of Classification Search
CPC ........ A61F 9/00; A61F 9/0008; A61F 9/0017; A61F 9/0026; A61F 9/00772;
(Continued)

(56) References Cited

U.S. PATENT DOCUMENTS 3,817,248 A * 6/1974 Buckles .................... A61F 6/14
                                              424/430
3,828,777 A   8/1974 Ness ............................ 424/427
(Continued)

FOREIGN PATENT DOCUMENTS

CA   2829533 A1   8/2006
CN   201469516 U  5/2010
(Continued)

OTHER PUBLICATIONS

Supplementary European Search Report dated Jul. 25, 2016 for European Patent Application No. 14740620.
(Continued)

*Primary Examiner* — Shefali D Patel
(74) *Attorney, Agent, or Firm* — Polsinelli PC

(57) ABSTRACT

This invention is in the field of medical intervention related to the lacrimal system. The invention relates to a lacrimal system device and methods of using the device for drug delivery to an eye, sinuses and/or periocular tissues.

29 Claims, 13 Drawing Sheets

(51) Int. Cl.
*A61M 31/00* (2006.01)
*A61K 9/00* (2006.01)

(52) U.S. Cl.
CPC ... *A61M 31/002* (2013.01); *A61F 2250/0003* (2013.01); *A61K 9/0048* (2013.01); *A61M 2205/0216* (2013.01); *A61M 2210/0612* (2013.01)

(58) Field of Classification Search
CPC .......... A61F 2250/0003; A61F 9/00736; A61F 2210/0057; A61F 2210/0061; A61F 2210/0066; A61F 2250/0067; A61F 2250/0068; A61M 31/00; A61M 31/002; A61M 2210/0612; A61M 2205/0216
See application file for complete search history.

(56) References Cited

U.S. PATENT DOCUMENTS

| | | | |
|---|---|---|---|
| 3,962,414 A * | 6/1976 | Michaels | A61F 9/0017 424/469 |
| 4,468,816 A | 9/1984 | Kaufer | |
| 4,658,816 A | 4/1987 | Ector, Jr. | |
| 4,781,675 A | 11/1988 | White | |
| 5,318,513 A | 6/1994 | Leib et al. | |
| 5,410,016 A | 4/1995 | Hubbell et al. | 528/354 |
| 5,437,625 A | 8/1995 | Kurihashi | |
| 5,836,935 A | 11/1998 | Ashton et al. | |
| 6,152,916 A | 11/2000 | Bige | |
| 6,196,993 B1 | 3/2001 | Cohan et al. | |
| 6,881,198 B2 * | 4/2005 | Brown | A61F 9/00781 604/10 |
| 7,066,904 B2 | 6/2006 | Rosenthal et al. | |
| 8,034,370 B2 | 10/2011 | Shiah et al. | 424/428 |
| 8,409,606 B2 | 4/2013 | Sawhney et al. | |
| 8,563,027 B2 | 10/2013 | Jarrett et al. | |
| 2007/0298075 A1 | 12/2007 | Borgia et al. | 424/428 |
| 2008/0086101 A1 * | 4/2008 | Freilich | A61F 9/0017 604/294 |
| 2008/0181930 A1 | 7/2008 | Rodstrom et al. | 424/427 |
| 2008/0199510 A1 | 8/2008 | Ruane et al. | |
| 2009/0104243 A1 | 4/2009 | Utkhede et al. | |
| 2009/0187098 A1 | 7/2009 | Makower et al. | |
| 2009/0306608 A1 | 12/2009 | Li et al. | |
| 2010/0034870 A1 | 2/2010 | Sim et al. | 424/427 |
| 2010/0179468 A1 | 7/2010 | Becker | |
| 2010/0274204 A1 * | 10/2010 | Rapacki | A61F 9/00772 604/285 |
| 2011/0251568 A1 * | 10/2011 | Beeley | A61F 9/0017 604/294 |
| 2011/0301555 A1 | 12/2011 | Gonzalez-Zugasti et al. | |
| 2012/0095439 A1 * | 4/2012 | de Juan, Jr. | A61F 9/0017 604/506 |
| 2013/0023837 A1 | 1/2013 | Becker | |
| 2014/0296834 A1 | 10/2014 | Moss et al. | |
| 2014/0364891 A1 | 12/2014 | Mendius et al. | |
| 2018/0344524 A1 | 12/2018 | Kahook | |
| 2019/0274877 A1 | 9/2019 | Schieber et al. | |

FOREIGN PATENT DOCUMENTS

| | | |
|---|---|---|
| EP | 1891942 B1 | 3/2010 |
| EP | 1891942 B1 | 3/2010 |
| JP | 2006-525953 | 11/2006 |
| JP | 2012-046530 | 3/2012 |
| JP | 2012-515628 | 7/2012 |
| TW | 201212962 A | 4/2012 |
| WO | 0071062 A1 | 11/2000 |
| WO | WO 02/056863 | 12/2001 |
| WO | 2008024982 A2 | 2/2008 |
| WO | 2009032328 A1 | 3/2009 |
| WO | WO/2009/032328 | 3/2009 |

OTHER PUBLICATIONS

Fleisher, D. et al. (1996) "Improved oral drug delivery: solubility limitations overcome by the use of prodrugs," *Advanced Drug Delivery Reviews* 19(2), 115-130.

Mooberry, S. L. et al. (1995) "Tubercidin stabilizes microtubules against vinblastine-induced depolymerization, a taxol-like effect," *Cancer Letters* 96(2), 261-266.

Murube, J. et al. (2003) "Subcutaneous abdominal artificial tears pump-reservoir for severe dry eyes," *Orbit* 22(1), 29.

Ro, A. J. et al. (2012) "Morphological and degradation studies of sirolimus-containing poly(lactide-co-glycolide) discs," *Journal of Biomedical Materials Research Part B: Applied Biomaterials* 100B(3), 767-777.

Smith, C. D. et al. (1994) "A sensitive assay for taxol and other microtubule-stabilizing agents," *Cancer Letters* 79(2), 213-219.

PCT International Search Report of International Application No. PCT/US2014/011477 dated Dec. 1, 2014.

* cited by examiner

Prior Art

LACRIMAL SYSTEM DRUG DELIVERY DEVICE

CROSS-REFERENCE TO RELATED APPLICATIONS

The present application is a 371 national entry of PCT/US2014/011477, filed Jan. 14, 2014, which claims the benefit of U.S. Provisional Patent Application No. 61/752,742, filed on. Jan. 15, 2013, which is incorporated herein by reference.

FIELD OF THE INVENTION

This invention is in the field of medical intervention related to the lacrimal system. The invention relates to a lacrimal system device and methods of using the device for drug delivery to the eye, sinuses and/or periocular tissues.

BACKGROUND OF THE INVENTION

A variety of challenges face patients and physicians in the area of ocular and respiration disease or disorder management, including adequate drug delivery to the eyes or nasal passage and treatment of dry eyes. In ocular management, for example, many current ocular drug delivery systems require repetitive manual drug administration and are often ineffective due to a lack of patient compliance or inadequate drug concentrations reaching the eye. Many current tear flow blockage techniques also have drawbacks, including being irreversible in nature.

A previously used approach of drug delivery to an eye or periocular tissues can be to place a removable, drug-releasing punctal implant into a punctum. It is believed that by allowing for the sustained release of one or more drugs, the present punctal implants can overcome some of the drawbacks associated with current drug administration (i.e., manual drop instillation), such as poor patient compliance, waste, untimely application, or non-localized delivery. One approach to blocking of tear flow from the eye is to place a removable, but retainable, punctal implant into the punctum, commonly called punctal plugs. Such punctal plugs have been suggested to provide an avenue for extended release drug delivery, however they suffer from several drawbacks including: dislodgement and displacement (especially if a patient rubs the eye or lid too vigorously or sneezes), limited medication reservoir capacity, and uneven delivery of therapeutic agents in patients with poor tear production as agent dispersal is dependent upon distribution via dilution in available tears on the tear film of the eye. What is needed is a device that can supply long term, steady release of therapeutic agents to treat subjects in need of delivering active agents to the eye and/or periocular tissues.

SUMMARY OF THE INVENTION

This invention is in the field of medical intervention related to the lacrimal system. The invention relates to a lacrimal system device and methods of using the device for drug delivery to the eye, sinuses and/or periocular tissues.

In one embodiment, the invention relates to a lacrimal system drug delivery device, comprising: a) a reservoir having a loading port and an exit port wherein said reservoir has elastic properties, b) a first tube connected to said exit port, and c) a second tube comprising a flow limiting port connected to said first tube. In one embodiment, said reservoir has self-compression properties. In another embodiment, said first tube and second tube comprise one continuous tube. In one embodiment, said first and second tubes are one continuous tube that contains a flow limiting port on the distal end of said device. In another embodiment, said device comprises a second set of a first tube connected to said exit port, and a second tube comprising a flow limiting port connected to said first tube. In one embodiment, said device further comprises a third tube connected to said loading port. FIG. 3A shows the inflated device by itself. FIG. 3B shows the major parts of the lacrimal system with which the device interacts. FIG. 3C shows an embodiment of the device, where there are two sets of tubes extending through each lacrimal duct to each punctum (superior punctum and an inferior punctum, upper punctum and a lower punctum, respectively). The device may have one or two sets of tubes. FIG. 3D show an embodiment of the device with two sets of tubes, but without the third flushing/refilling tube. FIG. 3E shows a preferred embodiment, a device with a single set of tubes terminating in a flow limiting port 5, said port terminates in the upper (superior) punctum. FIG. 3F shows the device with a single set of tubes terminating in a flow limiting port 5, said port terminates in the lower (inferior) punctum. In one embodiment, said device further comprises an internal spring connected to an internal plunger connected to said exit port. In one embodiment, said internal plunger enables the constant release of said composition without relying on said elastic reservoir. In one embodiment, nitinol wire (or other material) springs are used internal to the lacrimal portion of the device that pulls an internal plunger towards the distal opening as fluid is released to allow for constant fluid delivery without relyaing on a constant pressure elastomeric balloon. In one embodiment, said device further comprises a microelectromechanical systems (MEMS) spring pressure regulator. In one embodiment, said elastic reservoir further comprises a fluid comprising a composition with an active ingredient. In one embodiment, said elastic reservoir enables anatomical fixation. In one embodiment, said anatomical fixation is a device retention feature, much like a foley catheter retention feature. In one embodiment, said exit port is connected to an internal plunger. In one embodiment, said exit port is connected to internal springs connected to said internal plunger. In one embodiment, said device further comprise a microelectromechanical systems spring pressure regulator. In one embodiment, said device is made of bioerodible materials. In one embodiment, said device is made of medical grade materials. In one embodiment, said flow limiting port comprises a hole. In one embodiment, said flow limiting port comprises a filter. In one embodiment, said flow limiting port comprises at least one ePTFE membrane. In one embodiment, said ePTFE membranes may be used to regulate flow out of the distal end of said device. For example, ePTFE with 0.0003"+/−0.0001" (0.00762 mm+/−0.00254 mm) thickness and with a porosity of 80%+/−10% and a mean flow pore size of 0.2 to 0.5 micron. In one embodiment, one or more layers of ePTFE material can be used for flow regulation. In one embodiment, the flow of said fluid out of said device is gravity dependent. In one embodiment, the flow of said fluid out of said device is limited by a gravity dependent valve. In one embodiment, the flow of said fluid out of said device is controlled by a cut-off valve that is accessible by an operator (patient or physician) to decrease flow at given times of the day when treatment might not be needed (while sleeping for example). In one embodiment, the elastic reservoir will deliver fluid+/−active ingredients to the ocular surface at a fixed rate between 0.1 microliters and 30.0 microliters per day for a minimum of one week. In another embodiment, the delivery is achieved for a minimum of 60 days.

In another embodiment, the invention relates to a method of treatment, comprising: a) providing: i) a subject comprising lacrimal ducts and a lacrimal sac, ii) a lacrimal system drug delivery device, comprising: A) a elastic reservoir comprising a composition with at least one active ingredient, wherein said reservoir is capable of insertion inside said lacrimal sac, B) a first tube with a lumen extending from said elastic reservoir through either the upper or lower of the lacrimal ducts from within the naso-lacrimal duct, and C) a second tube with a flow limiting port connected to said first tube, wherein said second tube terminates with said flow limiting port in a punctum in contact with the tear film of the eye, b) inserting said drug delivery device into said lacrimal system; and c) administering said composition to said subject using said lacrimal system drug delivery device. In one embodiment, said reservoir has self-compression properties. In another embodiment, said first tube and second tube comprise one continuous tube. In another embodiment, said device comprises a second set of a first tube connected to said exit port and a second tube comprising a flow limiting port connected to said first tube wherein said second set second tube terminates with said flow limiting port in the other punctum in contact with the tear film of the eye. In one embodiment, said device further comprises a third tube connected to said elastic reservoir, wherein said third tube extends from said elastic reservoir into the nasolacrimal duct wherein it terminates. In one embodiment, said third tube that extends through the larcrimal duct and up to the nasal opening of the duct. In one embodiment, said device further comprises a cut-off valve. In one embodiment, said device comprises bioerodible materials. In one embodiment, said device comprises internal composition columns with said bioerodible materials. In one embodiment, the erosion of said bioerodible materials open up inlet pores sequentially allowing along said internal composition column which would enable for pulsed dosing of said composition. In one embodiment, said active ingredient consists of artificial tears, glaucoma drops, anti-inflammatory agents, nonsteroidal agents, antibiotics, biologics, proteins, aptamers, nucleic acids, cytokines, plasma, sympahtomemetics, parasympathomemetics, prostaglandin analogues, beta blockers, alpha-agonists, anti-VEGF agents and other agents known to treat diseases of the eye or periocular tissues. In one embodiment, said elastic reservoir may be accessed through said third tube for the process of flushing and refilling. In one embodiment, the flow of said fluid out of said device is controlled by a cut-off valve that is accessible by an operator to decrease flow at given times when treatment is not desired. In one embodiment, said flow limiting port regulates the flow of said composition from said device. In one embodiment, said flow limiting port comprises at least one ePTFE membrane. For example, ePTFE with 0.0003"+/−0.0001" (0.00762 mm+/−0.00254 mm) thickness and with a porosity of 80%+/−10% and a mean flow pore size of 0.2 to 0.5 micron. In one embodiment, said flow limiting port comprises at least one layer of ePTFE material. In one embodiment, nano to micron size holes at the tip of the device are used to control egress of fluid rather than ePTFE material. In one embodiment, the elastic reservoir will deliver fluid+/− active ingredients to the ocular surface at a fixed rate between 0.1 microliters and 30.0 microliters per day for a minimum of one week. In another embodiment, the delivery is achieved for a minimum of 60 days.

In one embodiment, the invention relates to a lacrimal system drug delivery device, comprising: a) an reservoir having a loading port and an exit port, b) a first tube connected to said exit port, and c) a second tube comprising a flow limiting port connected to said first tube. In one embodiment, said first and second tubes comprise one continuous tube. In one embodiment, said reservoir has self-compression properties. In one embodiment, said loading and exit port are the same port. In one embodiment, said reservoir comprises a nanoporous material. In one embodiment, said reservoir comprises a microrous material. In one embodiment, the balloon component 1 of the device may be designed only for fixation and not delivery (like foley catheter retention feature). In one embodiment, nitinol wire (or other material) springs 10 are used internal to the lacrimal portion of the device that pulls an internal plunger 8 towards the distal opening as fluid is released to allow for constant fluid delivery without relying on a constant pressure elastomeric balloon 1. In one embodiment, the device comprises bioerodible or biodegradable materials 6. In one embodiment, said bioerodible 6 or biodegradable materials 6 open up inlet pores sequentially allowing along the internal fluid column which would enable for pulsed dosing. In one embodiment, the device further comprises a microelectromechanical systems (MEMS) spring pressure regulator 12. In one embodiment, ePTFE membranes 7 may be used to regulate flow out of the distal end of said device. For example, ePTFE with 0.0003"+/−0.0001" (0.00762 mm+/−0.00254 mm) thickness and with a porosity of 80%+/−10% and a mean flow pore size of 0.2 to 0.5 micron. In one embodiment, one or more layers of ePTFE material can be used for flow regulation. FIG. 5 shows shows an angled view of the device. FIG. 6 shows an angled view of the device. FIG. 7 shows a tube distal end close-up. FIGS. 8A&B show one embodiment of the device. FIG. 8A shows the device consisting of a microporous balloon 1 that can deliver drug directly to tissue spaces such as sinuses. In contains a tube (3, 2) with a flow limiting port/exit port 5 which may or may not contain a distal membrane 7 which can serve as a simple filling port 7 (located in the punctum or in the conjunctiva/caruncle or surrounding tissues) to refill the microporous balloon 1 as needed. The balloon 1 then oozes out medication/fluid to targeted tissues. FIG. 8B shows that a nitinol cage 13 or other structural features may serve to exert pressure on the microporous balloon/reservoir 1. Instead of drug/composition being delivered only through the distal part 7, this option gives us the capability to deliver drug directly from the reservoir 1 to surrounding tissues with or without delivery through the distal part as well. There are certain diseases that would benefit from this approach, like chronic sinusitis. FIG. 9 shows a device where there is a miroporous balloon/elastic reservoir 1 and a distal membrane 7 where the first tube 2 contains bio erodible elements 6, and an internal plunger 8, and an exit port 9 is connected to internal springs 10 connected to said internal plunger 8, microelectromechanical systems spring pressure regulator 12, and bioerodible materials 6 open up inlet pores sequentially allowing along said internal composition column which would enable for pulsed dosing of the active agent composition. FIG. 10 shows one embodiment of the device where a separate nitinol device 13 is constructed to surround the reservoir 1 prior to filling so that the nitinol cage 13 contains straight wires. Once filled, the reservoir 1 pushes the nitinol out and the nitinol then acts on the non-elastic or semi-elastic material to slowly push fluid out towards the flow limiting membrane 7 at the top (exit port). In one embodiment the device comprises a reservoir and a first tube. In one embodiment, the device comprises a nonelastic reservoir that is contained within surrounding material that allows for compression of said reservoir. In one embodiment, a nitinol wire, spring or cage may be used to provide the compression of said reservoir. In one embodiment, the reservoir is substantially nonelastic. In one embodiment, said reservoir is made from a microporous or naonoporous material. In one embodiment, the composition within said reservoir is released through the pores of the reservoir material. In some embodiments, the device comprises a protective sleeve be placed over said reservoir. In one embodiment, said sleeve protects against leaks entering the nasal duct or other tissue compartments. In one embodiment, said device contains fluorescent material or coloring to allow for detection and postion confirmation by the user (physician or patient). In one embodiment, said reservoir is implanted within the sinuses surrounding the eye. In one embodiment, the punctal portion or distal end allows for filling the elastic reservoir with medication, but the elastic reservoir sits in a sinus and allows for delivery of drug through a microporous balloon. In one embodiment, the punctal portion is implanted through the caruncle or through the conjunctiva (similar to implantation of a jones tube) and allow for the microporous balloon pump to deliver drug directly to the sinus or other tissue areas surrounding the eye. In another embodiment, the device delivers medication through a microporous reservoir in addition to the primary embodiment that delivers to a tube with a hole positioned at the punctum. In one embodiment, the compressed reservoir will deliver fluid+/−active ingredients to the ocular surface at a fixed rate between 0.1 microliters and 30.0 microliters per day for a minimum of one week. In another embodiment, the delivery is achieved for a minimum of 60 days.

In another embodiment, the invention relates to a method of treatment, comprising: a) providing: i) a subject comprising lacrimal ducts, ii) a lacrimal system drug delivery device, comprising: A) a reservoir comprising a composition with at least one active ingredient, wherein said reservoir is capable of insertion inside said tissues surrounding the eye, including, but not limited to the lacrimal sac, sinuses, and punctual area, B) a first tube with a lumen extending from said reservoir through either the upper or lower of the lacrimal ducts from within the naso-lacrimal duct, and C) a second tube, connected to said first tube, with a flow limiting port connected to said first tube, wherein said second tube terminates with said flow limiting port in a punctum in contact with the tear film of the eye, b) inserting said drug delivery device into said lacrimal system; and c) administering said composition to said subject using said lacrimal system drug delivery device. In one embodiment, said reservoir has self-compression properties. In one embodiment the device comprises a reservoir and a first tube. In one embodiment, the device comprises a nonelastic reservoir that is contained within surrounding material that allows for compression of said reservoir. In one embodiment, a nitinol wire, spring or cage may be used to provide the compression of said reservoir. In one embodiment, the reservoir is substantially nonelastic. In one embodiment, said reservoir is made from a microporous or naonoporous material. In one embodiment, the composition within said reservoir is released through the pores of the reservoir material. In some embodiments, the device comprises a protective sleeve be placed over said reservoir. In one embodiment, said sleeve protects against leaks entering the nasal duct or other tissue compartments. In one embodiment, said device contains fluorescent material or coloring to allow for detection and postion confirmation by the user (physician or patient). In one embodiment, said reservoir is implanted within the sinuses surrounding the eye. In one embodiment, the punctal portion or distal end allows for filling the elastic reservoir with medication, but the elastic reservoir sits in a sinus and allows for delivery of drug through a microporous balloon. In one embodiment, the punctal portion is implanted through the caruncle or through the conjunctiva (similar to implantation of a jones tube) and allow for the microporous balloon pump to deliver drug directly to the sinus or other tissue areas surrounding the eye. In another embodiment, the device delivers medication through a microporous reservoir in addition to the primary embodiment that delivers to a tube with a hole positioned at the punctum. In one embodiment, the reservoir will deliver fluid+/−active ingredients to the ocular surface at a fixed rate between 0.1 microliters and 30.0 microliters per day for a minimum of one week. In another embodiment, the delivery is achieved for a minimum of 60 days.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "patient" or "subject" refers to any living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

"Prevention" or "preventing" as used herein, includes, but is not limited to: (1) inhibiting the onset of a disease in a subject or patient which may be at risk and/or predisposed to the disease, wherein such inhibition may be either partial or complete, but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

As used herein, the terms "medication" or "therapeutic agent" refer to any compound and/or molecule that treats or prevents or alleviates the symptoms of disease or condition, including, but not limited to, a drug or pharmaceutical composition. Medication is considered to be delivered or present in therapeutically effective amounts or pharmaceutically effective amounts.

"Therapeutically effective amounts" or "pharmaceutically effective amounts", as used herein, means that amount which, when administered to a subject or patient for treating a disease, is sufficient to effect such treatment for the disease or to ameliorate one or more symptoms of a disease or condition (e.g. ameliorate pain).

As used herein, the terms "treat" and "treating" are not limited to the case where the subject (e.g. patient) is cured and the disease is eradicated. Rather, treatment may also merely reduce symptoms, improves (to some degree) and/or delays disease progression among other effects. It is not intended that treatment be limited to instances wherein a disease or affliction is cured. It is sufficient that symptoms are reduced.

As used herein, the terms "medical device," "implant," "device," "medical device," "medical implant," "implant/device," and the like are used synonymously to refer to any object that is designed to be placed partially or wholly within a patient's body for one or more therapeutic or prophylactic purposes such as for tissue augmentation, contouring, restoring physiological function, repairing or restoring tissues damaged by disease or trauma, and/or delivering therapeutic agents to normal, damaged or diseased organs and tissues. While medical devices are normally composed of biologically compatible synthetic materials (e.g., medical-grade stainless steel, nitinol, titanium and other metals; exogenous polymers, such as polyurethane, silicone, PLA, PLGA, PGA, PCL), other materials may also be used in the construction of the medical implant. While not limiting the present invention to any particular device, specific medical devices and implants that are particularly relevant to this invention include stents, punctal plugs, Crawford tubes, catheters, lacrimal tubes, ocular or other shunts, and drug delivery systems. In some embodiments, the device incorporates a contrast material or opaque materials that allow for visualization with standard imaging devices (for example, barium to allow for x-ray visualization).

As used herein, the term "medication reservoir" refers to any elastic structure containing medication or therapeutic agent. In preferred embodiments, the reservoir is made of stretchy plastics or silicones.

As used herein, the term "proximal" refers to a location situated toward a point of origin (e.g., between a physician and a lacrimal implant device).

As used herein, the term "distal" refers to a location situated away from a point of origin (e.g., behind a lacrimal implant device relative to a physician).

As used herein, the term "hydrogel" is used to refer to an absorbing or otherwise retaining material (e.g., adsorbing material), such as super-absorbent polymers, hydrocolloids, and water-absorbent hydrophilic polymers, for example. In some examples, the term "hydrogel" refers to super-absorbent polymer particles in a "dry or dehydrated" state, more specifically, particles containing from no water up to an amount of water less than the weight of the particles, such as less than about 5%, by weight, water. In some examples, the term "hydrogel" refers to a super-absorbent polymer in the "dry or dehydrated" state when the hydrogel is not expandable and also refers to its hydrated or expanded state, more specifically, hydrogels that have absorbed at least their weight in water, such as several times their weight in water. As the hydrogel material absorbs fluid, it size can increase and its shape can change to bias against at least a portion of a lacrimal canaliculus ampulla or lacrimal canaliculus wall, for example.

As used herein, the term "medicament" refers to any active agent that is suitable for use in medical treatment, such as a medicinal compound or drug.

As used herein, the term "active agent" refers to any molecular entity that exerts an effect on a living organism.

As used herein, the term "polymer" refers to any organic macromolecule containing one or more repeating units, as is well known in the art.

As used herein, a "copolymer" refers to any polymer in which there are at least two types of repeating units included. A copolymer can be a block copolymer, in which there are segments containing multiple repeating units of one type, bonded to segments containing multiple repeating units of a second type.

As used herein, the term "hydrophilic polymer" refers to any polymer that can be wetted by water, i.e., does not have a water-repellant surface. A hydrophilic polymer can absorb water to a small degree, for example about 0-100 wt % of water, but does not greatly swell in volume as does a hydrogel-forming polymer.

As used herein, the terms "implanted" refers to having completely or partially placed a device within a host. A device is partially implanted when some of the device reaches, or extends to the outside of, a host.

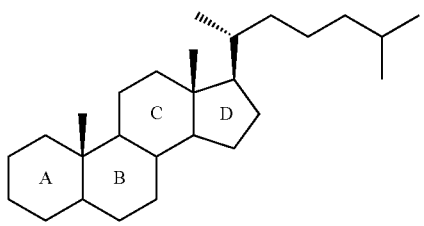

As used herein, the term "steroids" refers to any organic compound that contains a core composed of twenty carbon atoms bonded together that take the form of four fused rings: three cyclohexane rings (designated as rings A, B, and C in the figure to the right) and one cyclopentane ring (the D ring). The steroids vary by the functional groups attached to this four-ring core and by the oxidation state of the rings. Examples of steroids include, but are not limited to, the dietary fat cholesterol, the sex hormones estradiol and testosterone, and the anti-inflammatory drug dexamethasone.

As used herein, the term "non-steroidal anti-inflammatory agents," "nonsteroidal anti-inflammatory drugs," usually abbreviated to NSAIDs or NAIDs, but also referred to as nonsteroidal anti-inflammatory agents/analgesics (NSAIAs) or nonsteroidal Anti-inflammatory medicines (NSAIMs), refers to any drug with analgesic and antipyretic (fever-reducing) effects and which have, in higher doses, anti-inflammatory effects.

As used herein, the term "antibiotics" refers to any compound or substance that kills or inhibits the growth of bacteria, fungus, or other microorganism.

As used herein, the term "anti-inflammatory agent" refers to any substance or treatment that reduces inflammation.

As used herein, the term "immunosuppressant agents" refers to all drugs that inhibit or prevent activity of the immune system.

As used herein, the term "anti-neoplastic agents" refers to all drugs that prevent or inhibit the development, maturation, or spread of neoplastic cells.

As used herein, the term "prostaglandin analogues" refers to all molecules that bind to a prostaglandin receptor.

As used herein, the term "nitric oxide" or "nitrogen monoxide" refers to any binary diatomic molecule with the chemical formula NO.

As used herein, the term "endothelin" refers to any protein that consisting of 21 amino acid residues that are produced in various cells and tissues, that play a role in regulating vasomotor activity, cell proliferation, and the production of hormones, and that have been implicated in the development of vascular disease. For example, endothelin biological activity may include, but is not limited to, constrict blood vessels, raise blood pressure, decrease eye pressure, and protect neuronal tissues from degeneration.

As used herein, the term "corticosteroids" refers to a class of chemicals that includes any naturally produced steroid hormone or synthetic steroid hormone analogue. Corticosteroids are involved in a wide range of physiologic processes, including, but not limited to, stress response, immune response, and regulation of inflammation, carbohydrate metabolism, protein catabolism, blood electrolyte levels, and behavior.

As used herein, the term "antibody-based immunosuppresants" refers to any antibody (e.g., polyclonal, monoclonal, Fab etc) having an immunosuppressant activity As used herein, the term "release of an agent" refers to any presence of the agent, or a subcomponent thereof, emanating from an implant device.

As used herein, the terms "analogue or analog" refer to any chemical compound that is structurally similar to a parent compound but differs slightly in composition (e.g., one atom or functional group is different, added, or removed). An analogue may or may not have different chemical or physical properties than the original compound and may or may not have improved biological and/or chemical activity. For example, the analogue may be more hydrophilic, or it may have altered reactivity as compared to the parent compound. The analogue may mimic the chemical and/or biological activity of the parent compound (i.e., it may have similar or identical activity), or, in some cases, may have increased or decreased activity. The analogue may be a naturally or non-naturally occurring (e.g., recombinant) variant of the original compound. An example of an analogue is a mutein (i.e., a protein analogue in which at least one amino acid is deleted, added, or substituted with another amino acid). Other types of analogues include isomers (enantiomers, diastereomers, and the like) and other types of chiral variants of a compound, as well as structural isomers. The analogue may be a branched or cyclic variant of a linear compound. For example, a linear compound may have an analogue that is branched or otherwise substituted to impart certain desirable properties (e.g., improve hydrophilicity or bioavailability).

As used herein, the term "derivative" refers to any chemically or biologically modified version of a chemical compound that is structurally similar to a parent compound and (actually or theoretically) derivable from that parent compound. A "derivative" differs from an "analogue" in that a parent compound may be the starting material to generate a "derivative," whereas the parent compound may not necessarily be used as the starting material to generate an "analogue." An analogue may have different chemical or physical properties of the parent compound. For example, the derivative may be more hydrophilic or it may have altered reactivity as compared to the parent compound. Derivatization (i.e., modification) may involve substitution of one or more moieties within the molecule (e.g., a change in functional group). For example, a hydrogen may be substituted with a halogen, such as fluorine or chlorine, or a hydroxyl group (—OH) may be replaced with a carboxylic acid moiety (—COOH). The tem "derivative" also includes conjugates, and prodrugs of a parent compound (i.e., chemically modified derivatives that can be converted into the original compound under physiological conditions). For example, the prodrug may be an inactive form of an active agent. Under physiological conditions, the prodrug may be converted into the active form of the compound. Prodrugs may be formed, for example, by replacing one or two hydrogen atoms on nitrogen atoms by an acyl group (acyl prodrugs) or a carbamate group (carbamate prodrugs). More detailed information relating to prodrugs is found, for example, in Fleisher et al., Advanced Drug Delivery Reviews 19 (1996) 115 [1] incorporated herein by reference. The term "derivative" is also used to describe all solvates, for example hydrates or adducts (e.g., adducts with alcohols), active metabolites, and salts of the parent compound. The type of salt that may be prepared depends on the nature of the moieties within the compound. For example, acidic groups, for example carboxylic acid groups, can form, for example, alkali metal salts or alkaline earth metal salts (e.g., sodium salts, potassium salts, magnesium salts and calcium salts, and also salts with physiologically tolerable quaternary ammonium ions and acid addition salts with ammonia and physiologically tolerable organic amines such as, for example, triethylamine, ethanolamine or tris-(2-hydroxyethyl)amine). Basic groups can form acid addition salts, for example with inorganic acids such as hydrochloric acid, sulfuric acid or phosphoric acid, or with organic carboxylic acids and sulfonic acids such as acetic acid, citric acid, benzoic acid, maleic acid, fumaric acid, tartaric acid, methanesulfonic acid or p-toluenesulfonic acid. Compounds that simultaneously contain a basic group and an acidic group, for example a carboxyl group in addition to basic nitrogen atoms, can be present as zwitterions. Salts can be obtained by customary methods known to those skilled in the art, for example by combining a compound with an inorganic or organic acid or base in a solvent or diluent, or from other salts by cation exchange or anion exchange.

As used herein, the term "inhibitor" or "antagonist" refers to any agent that prevents a biological process from occurring and/or slows the rate and/or slows the degree of occurrence of a biological process. The process may be a general one such as scarring or refer to a specific biological action such as, for example, a molecular process resulting in release of a cytokine.

As used herein, the term "agonist" refers to any agent that stimulates a biological process or rate or degree of occurrence of a biological process. The process may be a general one such as scarring or refer to a specific biological action such as, for example, a molecular process resulting in release of a cytokine.

As used herein, the term "anti-microtubule agent" should be understood to include any protein, peptide, chemical, or other molecule that impairs the function of microtubules, for example, through the prevention or stabilization of polymerization. Compounds that stabilize polymerization of microtubules are referred to herein as "microtubule stabilizing agents." A wide variety of methods may be utilized to determine the anti-microtubule activity of a particular compound, including for example, assays described by Smith et al. (Cancer Lett. 79(2):213-219, 1994) [2] and Mooberry et al., (Cancer Lett. 96(2):261-266, 1995) [3] both incorporated herein by reference.

Any concentration ranges, percentage range, or ratio range recited herein are to be understood to include concentrations, percentages or ratios of any integer within that range and fractions thereof, such as one tenth and one hundredth of an integer, unless otherwise indicated. In addition, any number range recited herein relating to any physical feature, such as polymer subunits, size or thickness, are to be understood to include any integer within the recited range, unless otherwise indicated. It should be understood that the terms "a" and "an" as used above and elsewhere herein refer to "one or more" of the enumerated components. For example, "a" polymer refers to both one polymer or a mixture comprising two or more polymers. As used herein, the term "about" means±15%.

As used herein, the term "biomaterial" refers to any substance (other than drugs) or combination of substances synthetic or natural in origin, which can be used for any period of time, as a whole or as a part of a system which treats, augments, or replaces any tissue, organ, or function of the body.

As used herein, the term "biocompatibility" refers to the ability of a material to perform with an appropriate host response in a specific application.

As used herein, the term "elastic limit" or "yield strength" refers to the stress at which a material begins to deform plastically. Prior to the yield point the material will deform elastically and will return to its original shape when the applied stress is removed. Once the yield point is passed, some fraction of the deformation will be permanent and non-reversible.

As used herein, the term "elastic" refers to a material that with very large deformability when forces are applied on it with complete recoverability, meaning the object will return to its initial shape and size when these forces are removed. Such a feature has also been referred to as rubber elasticity. Molecular Requirements of such "elastic" materials: Material must consist of polymer chains, Need to change conformation and extension under stress. Polymer chains must be highly flexible. Need to access conformational changes (not w/ glassy, crystalline, stiff mat.) Polymer chains must be joined in a network structure. Need to avoid irreversible chain slippage (permanent strain). One out of 100 monomers must connect two different chains. Connections (covalent bond, crystallite, glassy domain in block copolymer) Examples of elastic polymers include rubber, latex, synthetic rubbers, neoprene, silicone and the like.

As used herein, the term "non-elastic" refers to a material that with low or no deformability when forces are applied on it. Beyond the strain limit, a non-elastic material will experience irreversible deformation. Polymer chains are not flexible and do not easily access conformational changes. These may undergo irreversible chain slippage (permanent strain) Examples include glass, hard plastics, amorphous glassy polymers and the like.

As used herein, the term "semi-elastic" refers to a material that with moderate deformability when forces are applied on it with complete recoverability, meaning the object will return to its initial shape and size when these forces are removed. There are a number of semi-elastic polymers. Examples of semi-crystalline polymers are linear polyethylene (PE), polyethylene terephthalate (PET), polytetrafluoroethylene (PTFE) or isotactic polypropylene (PP).

As used herein, the term "self-compression" refers to when a material is added to a reservoir and filled to distortion leading to elastic forces to compress material inside the reservoir. This self-compression provides a force to initiate distribution of the material within the reservoir out of the reservoir, either through a flow limiting port or through forced diffusion.

As used herein, the term "stent" refers to any artificial 'tube' inserted into a natural passage/conduit in the body to prevent, or counteract, a disease-induced, localized flow constriction. The term may also refer to a tube used to temporarily hold such a natural conduit open to allow access for surgery.

As used herein, the term "shunt" refers to any artificial 'tube' inserted into the body to create a hole or passage to allow movement of fluids between two areas. Said tube may be implanted temporarily or may be permanent.

As used herein, the term "Foley catheter" refers to a flexible tube that is often passed through the urethra and into the bladder. The tube has two separated channels, or lumens, running down its length. One lumen is open at both ends, and allows urine to drain out into a collection bag. The other lumen has a valve on the outside end and connects to a balloon at the tip; the balloon is inflated with sterile water, or other fluid/gas, when it lies inside the bladder, in order to stop it from slipping out.

As used herein, the term "catheter" refers to any tube that can be inserted into a body cavity, duct, or vessel. Catheters thereby allow drainage, administration of fluids or gases, or access by surgical instruments. The process of inserting a catheter is catheterization. In most uses, a catheter is a thin, flexible tube ("soft" catheter), though in some uses, it is a larger, solid ("hard") catheter. A catheter left inside the body, either temporarily or permanently, may be referred to as an indwelling catheter. A permanently inserted catheter may be referred to as a permcath.

As used herein, the term "microelectromechanical systems" or "MEMS" refers to technology of very small devices. MEMS are separate and distinct from the hypothetical vision of molecular nanotechnology or molecular electronics. MEMS are made up of components between 1 to 100 micrometres in size (i.e. 0.001 to 0.1 mm), and MEMS devices generally range in size from 20 micrometres (20 millionths of a metre) to a millimetre (i.e. 0.02 to 1.0 mm) They usually consist of a central unit that processes data (the microprocessor) and several components that interact with the surroundings such as microsensors.

As used herein, the term "PLGA or poly(lactic-co-glycolic acid)" refers to a copolymer and is approved for therapeutic devices by the United States Food and Drug Administration (FDA), owing to its biodegradability and biocompatibility. PLGA has been studied for slow drug release[4].

As used herein, the term "polyethylene glycol" (abbreviated PEG) refers to any polyether compound. For example, PEG is commercially available as polyethylene oxide (PEO) or polyoxyethylene (POE), depending on its molecular weight (Carbowax®).

DESCRIPTION OF THE FIGURES

The accompanying figures, which are incorporated into and form a part of the specification, illustrate several embodiments of the present invention and, together with the description, serve to explain the principles of the invention. The figures are only for the purpose of illustrating a preferred embodiment of the invention and are not to be construed as limiting the invention.

FIG. 1A shows a larger view of the eye, while

FIG. 3A shows the inflated device by itself. FIG. 3B shows the major parts of the lacrimal system with which the device interacts. FIG. 3C shows an embodiment of the device, where there are two sets of tubes extending through each lacrimal duct to each punctum (superior punctum and an inferior punctum, upper punctum and a lower punctum, respectively). The device may have one or two sets of tubes. FIG. 3D show an embodiment of the device with two sets of tubes, but without the third flushing/refilling tube. FIG. 3E shows a preferred embodiment, a device with a single set of tubes terminating in a flow limiting port 5, said port terminates in the upper (superior) punctum. FIG. 3F shows the device with a single set of tubes terminating in a flow limiting port 5, said port terminates in the lower (inferior) punctum.

FIG. 8A shows the device consisting of a microporous balloon 1 that can deliver drug directly to tissue spaces such as sinuses. In contains a tube (3, 2) with a flow limiting port/exit port 5 which may or may not contain a distal membrane 7 which can serve as a simple filling port 7 (located in the punctum or in the conjunctiva/caruncle or surrounding tissues) to refill the microporous balloon 1 as needed. The balloon 1 then oozes out medication/fluid to targeted tissues.

LIST OF REFERENCE NUMERALS

Figure 1A:
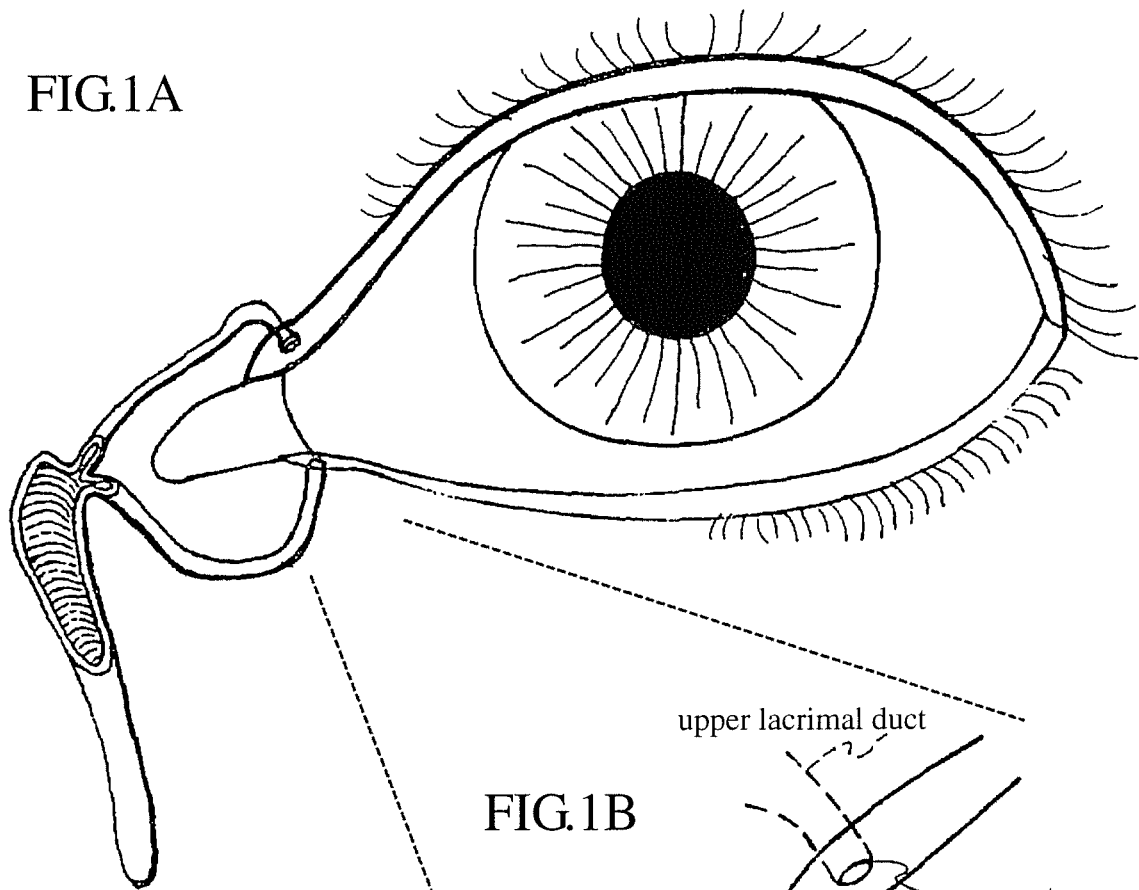
FIGS. 1A&B show an example of currently used punctal plugs inserted into the inferior punctum.
Figure 1B:
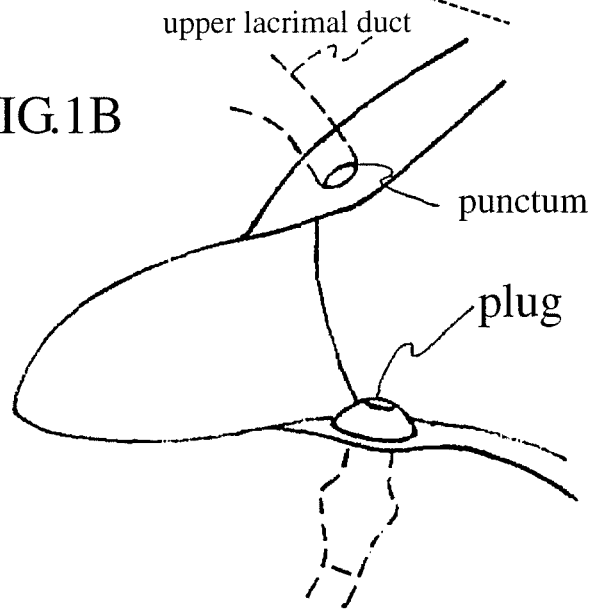
FIG. 1B shows an expanded view of an upper punctum and a lower punctum with a punctal plug. Some punctal plugs are used a medication release platforms, but contain a very limited reservoir and depend upon natural interaction with the tear film and tear distribution for dispersal of the therapeutic agent.

1 elastic reservoir
2 first tube
3 second tube
4 third tube
5 faceplate containing flow limiting capabilities
6 bio erodible elements
7 distal membrane
8 internal plunger
9 exit port
10 internal springs
11 internal plunger
12 microelectromechanical systems spring pressure regulator
13 nitinol cage
14 loading port
15 at least one hole
16 a filter
17 a gravity dependent valve
18 a cut-off valve
19 internal composition columns
20 inlet pores
21 at least one layer of ePTFE material

DETAILED DESCRIPTION OF THE INVENTION

In order to eye treat infection, inflammation of the eye, glaucoma and other ocular diseases or disorders, drugs are often required to be administered to the eye. A conventional method of drug delivery is by topical drop application to the eye's surface. Topical eye drops, though effective, can be inefficient. As one example, when an eye drop is instilled in an eye, it often overfills the conjunctival sac (i.e., the pocket between the eye and the lids) causing a substantial portion of the drop to be lost due to overflow of the lid margin and spillage onto the cheek. In addition, a large portion of the drop remaining on the ocular surface can be washed away into and through a lacrimal canaliculus, thereby diluting the concentration of the drug before it can treat the eye. Moreover, topically applied drugs often have a peak ocular effect for about two hours post-application, after which additional applications of the drugs should be, but are often not, administered to maintain the desired drug therapeutic benefit.

To compound ocular management difficulty, patients often do not use their eye drops as prescribed. This poor compliance can be due to, for example, an initial stinging or burning sensation caused by the eye drop and experience by a patient. Instilling eye drops in one's own eye can be difficult, in part because of the normal reflex to protect the eye. Therefore, one or more drops may miss the eye. Older patients may have additional problems instilling drops due to arthritis, unsteadiness, and decreased vision. Pediatric and psychiatric populations pose difficulties as well.

Conditions of dry eye have been treated by blocking the tear flow from the eye into and through the lacrimal canaliculus. This has involved closing the canalicular canal by stitching the punctal opening shut or by using electrical or laser cauterization to seal the punctal opening. Although such procedures can provide the desired result of blocking tear flow to treat a dry eye, they are unfortunately not reversible without reconstructive surgery.

In a field different from ocular management, control of respiration-related (e.g., allergies) diseases or disorders often requires repetitive manual digestion or other intake of a medication, and as such, can be ineffective due to a lack of patient compliance or non-localized drug delivery.

Therapeutic Devices

There have a variety of therapeutic devices designed to address eye and lacrimal system related conditions. Primary amongst them are lacrimal punctal plugs. There are several devices, which have useful features, yet do not have the advantages of the current invention.

In one reference, Sim, S. et al. "Composite Lacrimal Insert and Related Methods," United States Patent Application 20100034870 application Ser. No. 12/432,553, filed Apr. 29, 2009 [5], discloses a removable, drug-releasing lacrimal implant owned by QLT. The plug is implanted into a lacrimal punctum of a subject. Such a punctal plug comprise to a drug core that erodes with delivery to the tear film, dependent on tear movement to dissolution of the drug core. The drug core is sedentary and the tears are required to flow in and out of the reservoir for drug distribution. This application does not teach the elastic reservoir system and the active "pushing" of fluid into the tear film of the current invention.

In another reference, Hubbell, J. A. et al. "Photopolymerizable Biodegradable Hydrogels as Tissue Contacting Materials and Controlled-Release Carriers," U.S. Pat. No. 5,410,016 filed Mar. 1, 1993 [6], discloses a biodegradable PEG based system also used for punctal plug delivery owned by Ocular Therapeutix. This does not describe the device with an elastic reservoir of the current invention.

In another reference, Rodstrom, T. R. et al. "Punctal Plugs and Methods of Delivering Therapeutic Agents," United States Patent Application 20080181930 filed Jan. 30, 2008 [7], discloses another punctal plug drug delivery system with a matrix of a silicone and an ophthalmic drug with a parylene polymer coating on a portion of the outer surface. The method of drug delivery is passive utilizing the dissolution of the drug into the tear film of the eye. The plug and an extended portion, but lacks the reservoir of the current invention.

In another reference, Borgia, M. J. et al. "Punctal Plugs for the Delivery of Active Agents," United States Patent Application 20070298075 filed Jun. 7, 2007 [8], discloses another example of punctal plugs with slow release drug delivery. The reference does not describe reservoir of the current invention.

In another reference, Beeley, N. R. F. and Coldren, B. A. "Punctal Plugs for Controlled Release of Therapeutic Agents," United States Patent Application 20110251568 filed Mar. 8, 2011 [9], discloses several types of punctal plugs, but in one example, the plug includes an extended "reservoir" which is to be slightly permeable and extends into the lacrimal ducts. The reference does not describe an elastic reservoir or a reservoir located in the lacrimal sac of the current invention.

In another reference, Brubaker, M. J. et al. "Sustained Release Drug Delivery Devices," WIPO Patent Application WO/2002/056863 Application PCT/US2001/048804, filed Jul. 25, 2002 [10], discloses another plug device for distribution of a medication. The reference does not describe an elastic reservoir or a reservoir located in the lacrimal sac of the current invention.

In another reference, Rapacki, A. R. et al. "Lacrimal Implants and Related Methods," United States Patent Application 20100274204 filed Feb. 23, 2010 [11], discloses another lacrimal drug delivery device which is an extended version of a punctal plug, with an additional anchoring arm that extends down the lacrimal duct when inserted. The reference describes the use of "balloons" as structural elements to position the device, not as drug containing reservoirs. The reference does not describe an elastic reservoir or a reservoir located in the lacrimal sac of the current invention.

In another reference, Cohan, B. E. "Opthalmic Insert and Method for Sustained Release of Medication to the Eye," European Patent EP1891942B1 Application EP1178779A1, filed Apr. 7, 2000 [12], discloses an apparatus for intubation of lacrimal duct (lacrimal drainage pathway) for treatment of lacrimal duct obstruction. Additionally, the internal portion of the device may act as a reservoir of medication that may be released through a pore on the device in a controlled manner based upon a specific geometry of the device. This controlled rate is still based upon tear dissolution of the medication and penetration of the reservoir by the tear film. The reference does not describe an elastic reservoir or a reservoir located in the lacrimal sac of the current invention.

In another reference, Murube, J. et al. (2003) Subcutaneous Abdominal Artificial Tears Pump-Reservoir for Severe Dry Eyes, *Orbit* 22(1), 29 [13], discloses a study of an implanted pump-reservoir unit placed under the subcutaneous tissue of the abdomen for providing artificial tears to the ocular surface in patients with severe dry eye. While this system does provide for a reservoir, the system uses an electrical pump and the reservoir's location is far from the lacrimal sac. The reference does not describe an elastic reservoir or a reservoir located in the lacrimal sac of the current invention.

DETAILED DESCRIPTION OF A PREFERRED EMBODIMENT

The current invention involves an implanted medical device designed as a lacrimal system drug delivery device. It is a lacrimal system device with associated flexible elastic reservoir can be implanted so that the distal edge is proximate to the tear film abutting the upper or lower punctum and the opposite end is composed of a flexible material that forms an elastic reservoir (positioned in the lacrimal sac) that can be filled with an active ingredient, such as a drug or other therapeutic solution. Once filled, the active ingredient will be "pushed" from the elastic reservoir to the distal opening, which is proximate to the tear film. The drug then enters the tear film and is absorbed by eye tissues to treat various ocular diseases. The device may or may not also connect to the nasal cavity through the termination of the tear duct system. The egress of drug from the balloon of the device is entirely dependent on the elastic reservoir's effort to return to the uninflated state. No active pumps are needed. The ultimate goal of this device is to deliver drugs long term to the ocular surface in a regular and consistent manner. Other devices that deliver drug to the tear film using a punctal plug or lacrimal plug do so by a drug core that degrades after contact with the tear film.

While not limiting the current invention, one method of insertion of the device would be to introduce the collapsed device on the punctal side in an insertion method similar to the introduction of a Crawford tube. The collapsed reservoir of the device is envisioned to fit through the punctum and canaliculus wherein the reservoir of the device would reside in the lacrimal sac allowing for expansion when filled with a therapeutic agent. In one embodiment, a lubricant is coupled with the system to allow for smoother atraumatic insertion. In the embodiment, the device contains a further tube from the reservoir allowing access to the reservoir from the nasolacrimal duct for flushing and refilling. In one embodiment, a further tube could be accessed through various means including, but not limited to a small clip upon the tube, a groove in groove lock system, a kiss lock/coin purse system of closure, or complete closure or crimping of the end of the tube. While not limiting the device, it is envisioned that the device would conform the standard anatomical size variations. In one embodiment, the device could be used for subjects of various sizes and age ranges. In one embodiment, the device may not be appropriate in certain subjects, including, but not limited to subjects with trauma to the nasolacrimal system, subjects with chronic nasal inflammation, or dacryocystitis. Dacryocystitis is an inflammation of the nasolacrimal sac, frequently caused by nasolacrimal duct obstruction or infection. In one embodiment, the device functions and serves for at least two months or greater than sixty days. In the particular cases of treating dye eye or glaucoma, the device therapy would last at least two months. In the case of post-surgical treatment of conditions, such as cataracts, would involve treatment ranging of two to six week, possibly longer.

Figure 2:
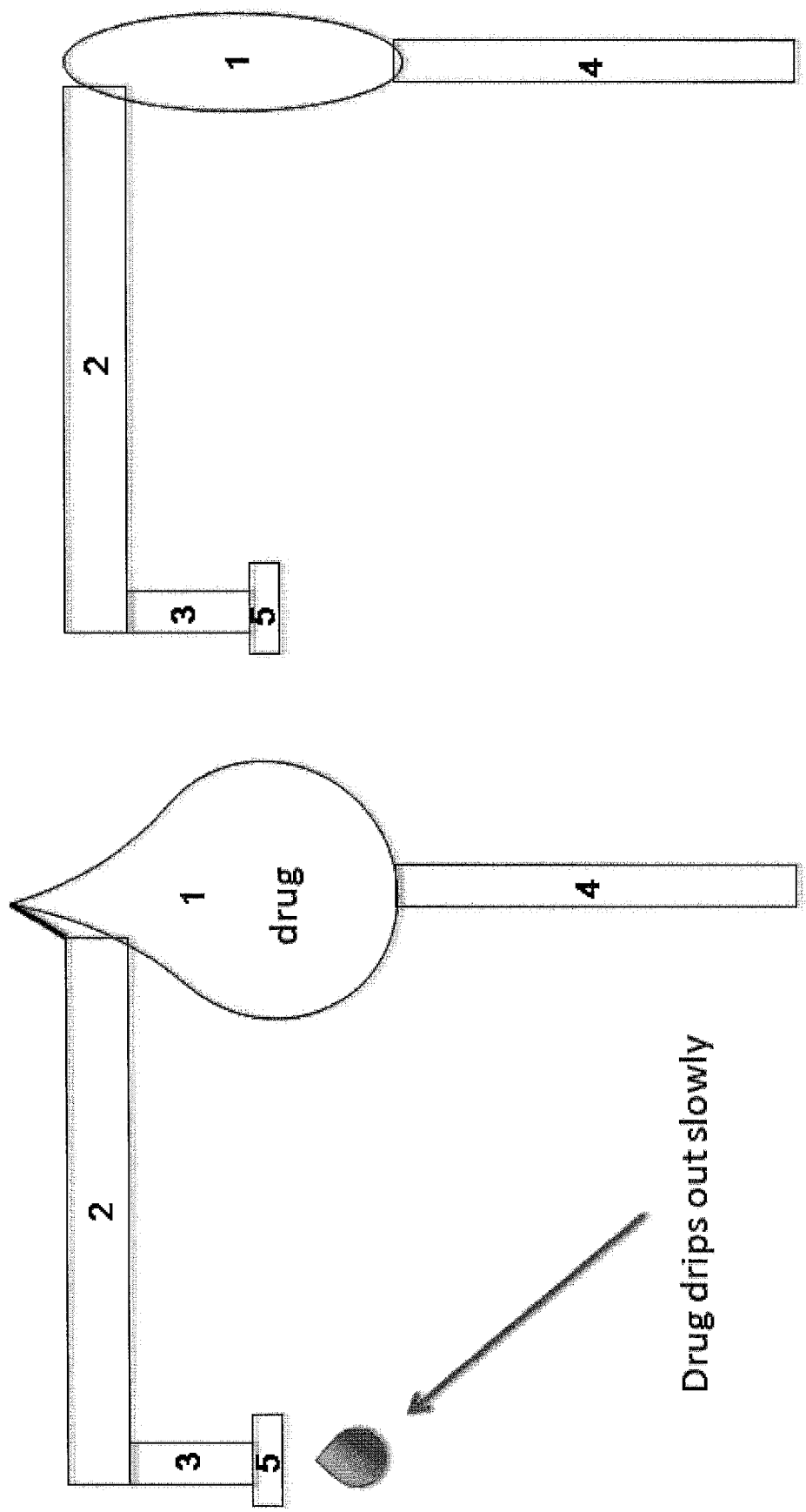
FIG. 2 shows an example of the current invention's design. This model shows both an inflated and depressed reservoir. This device provides for the controlled release of the therapeutic agent via a flow limited port attached to the tube portion that exits a punctum of the lacrimal system (shown in FIG. 3A-F).
Figure 3A:
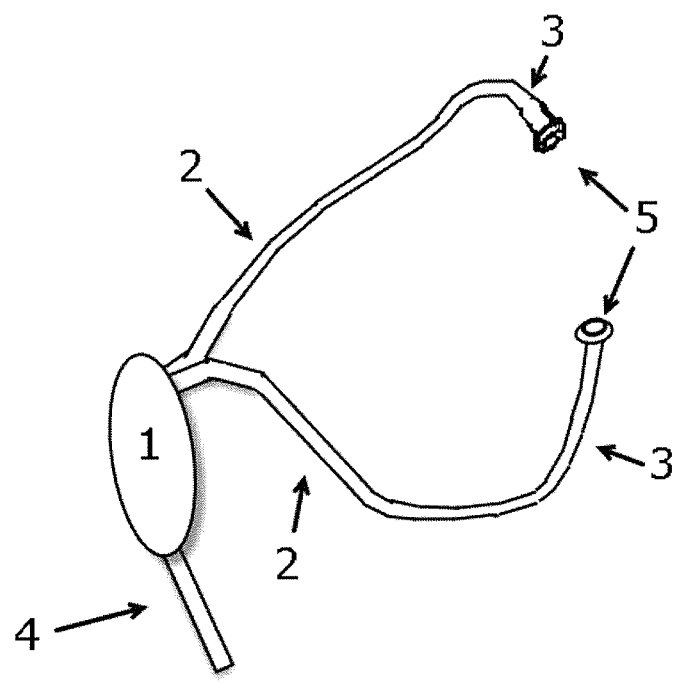
FIG. 3A-F shows examples of the inflated device properly inserted within the lacrimal system, portion of the lacrimal system, and the inflated device by itself.
Figure 3B:
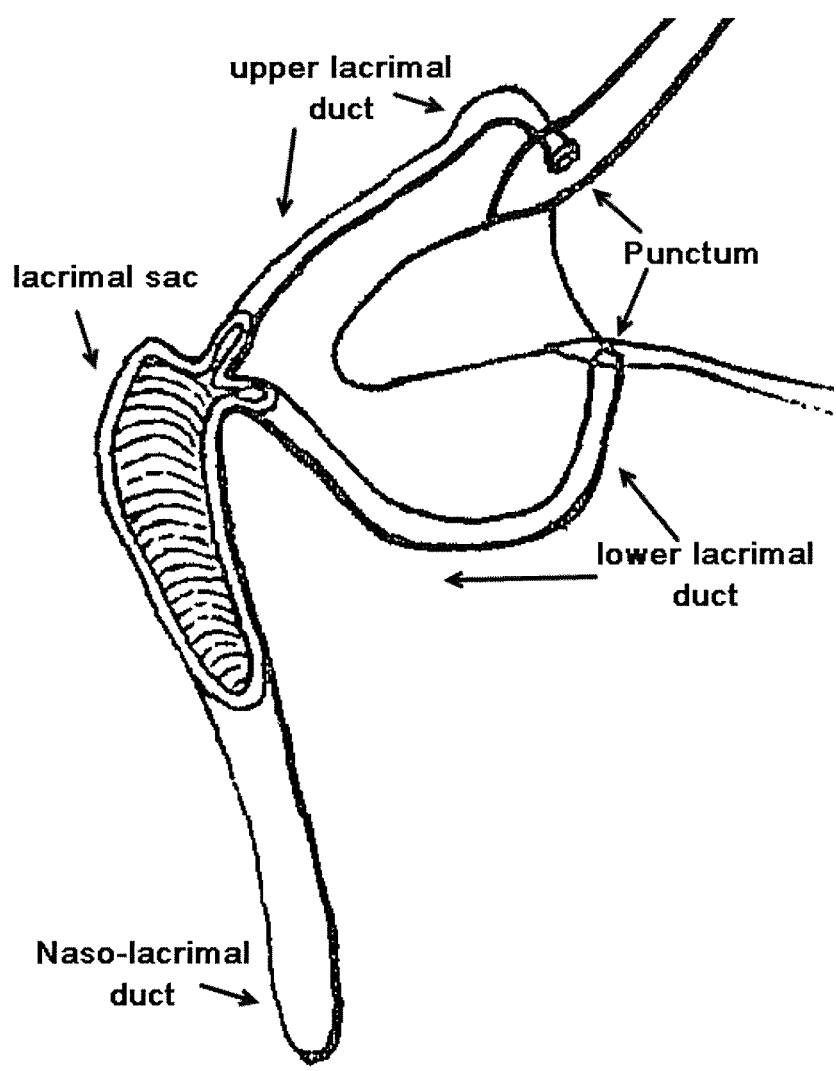
Figure 3C:
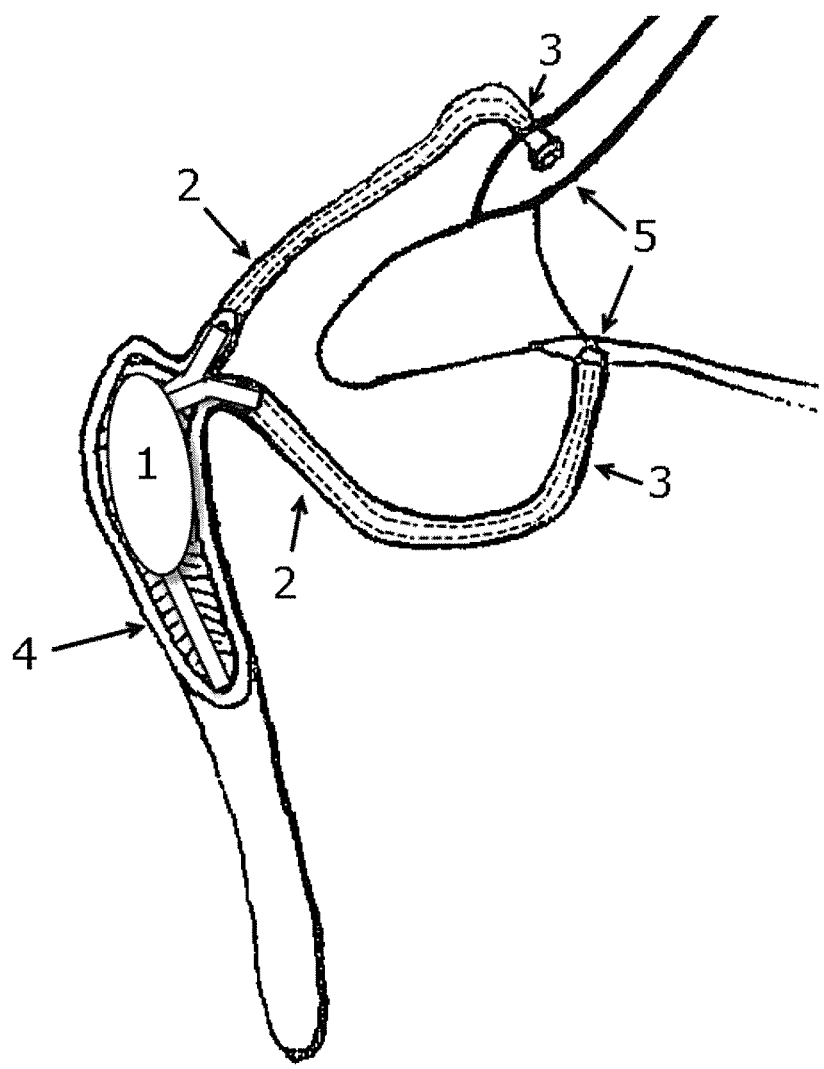
Figure 3D:
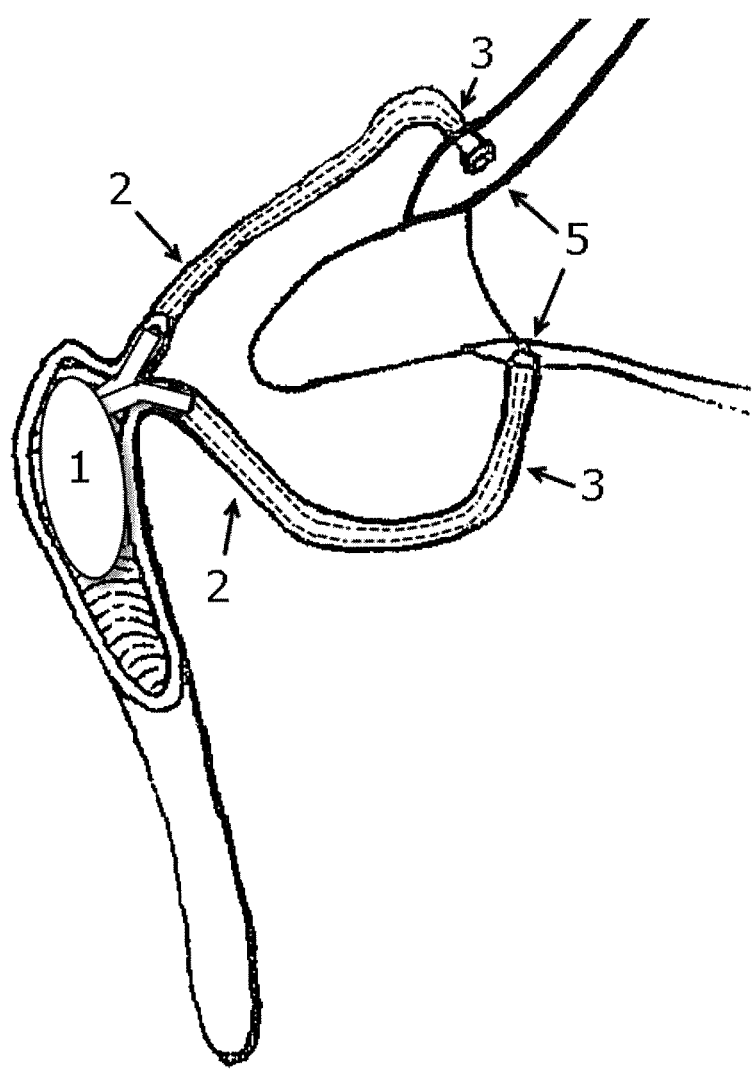
Figure 3E:
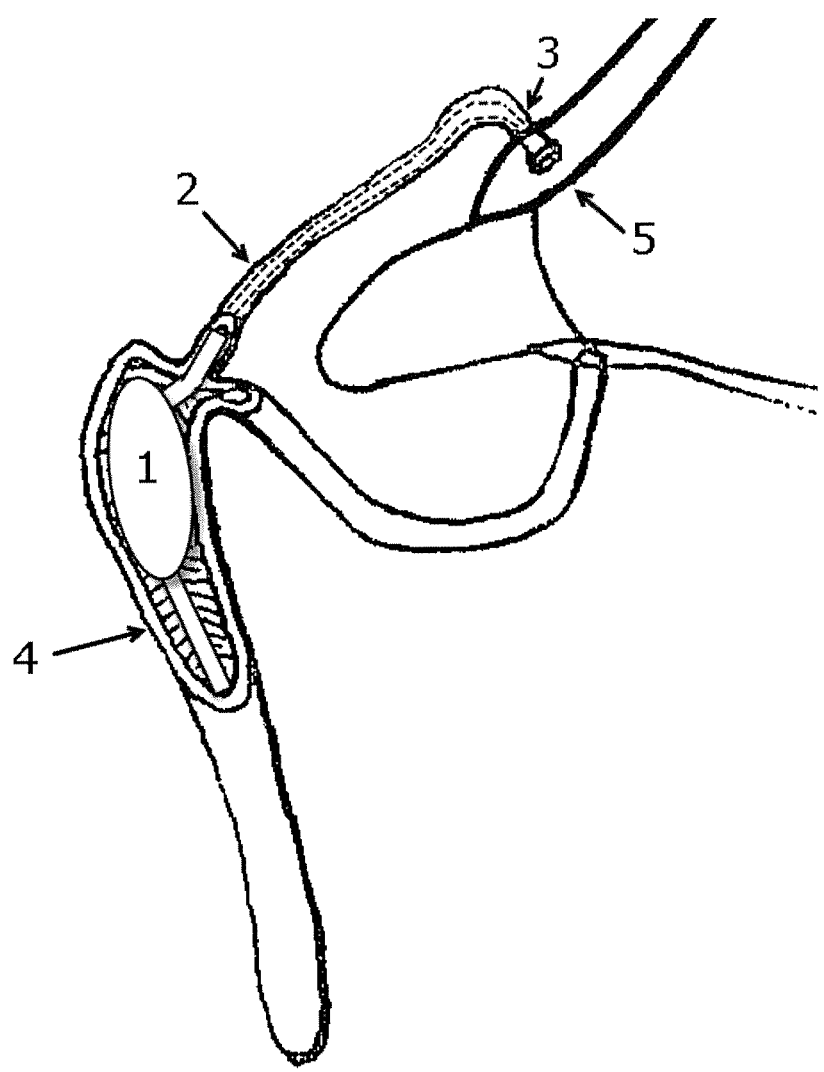
Figure 3F:
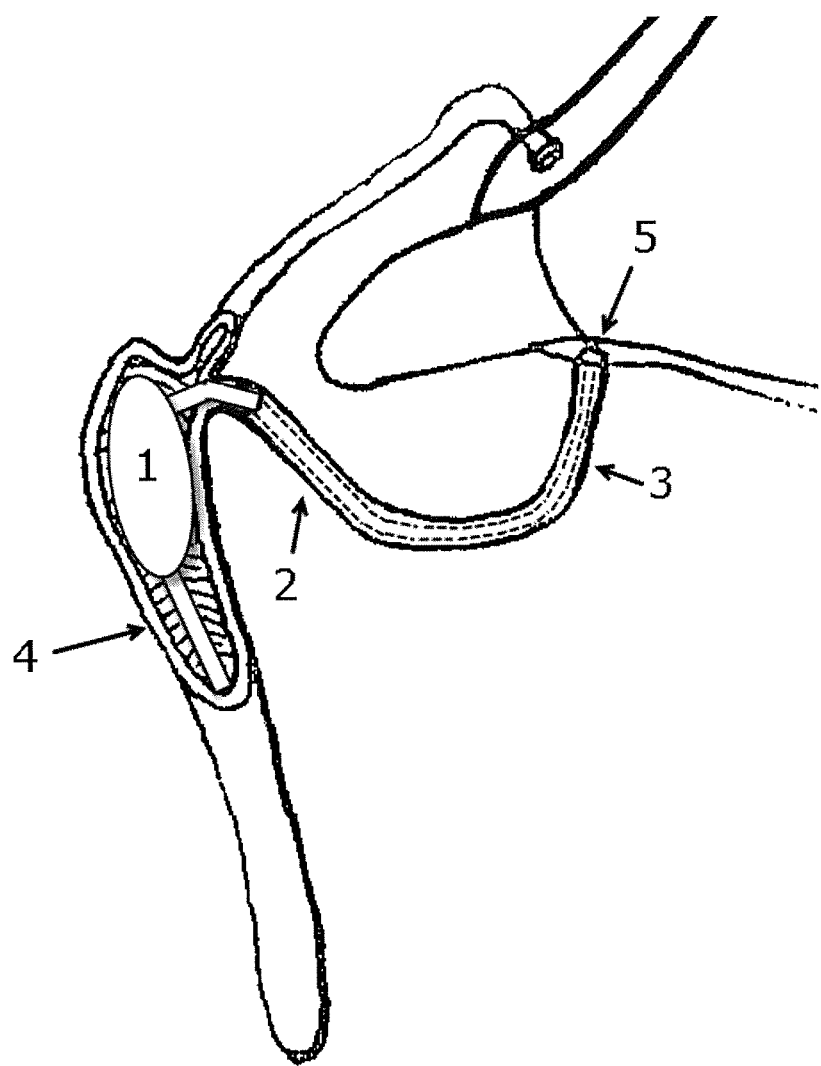
Figure 4:
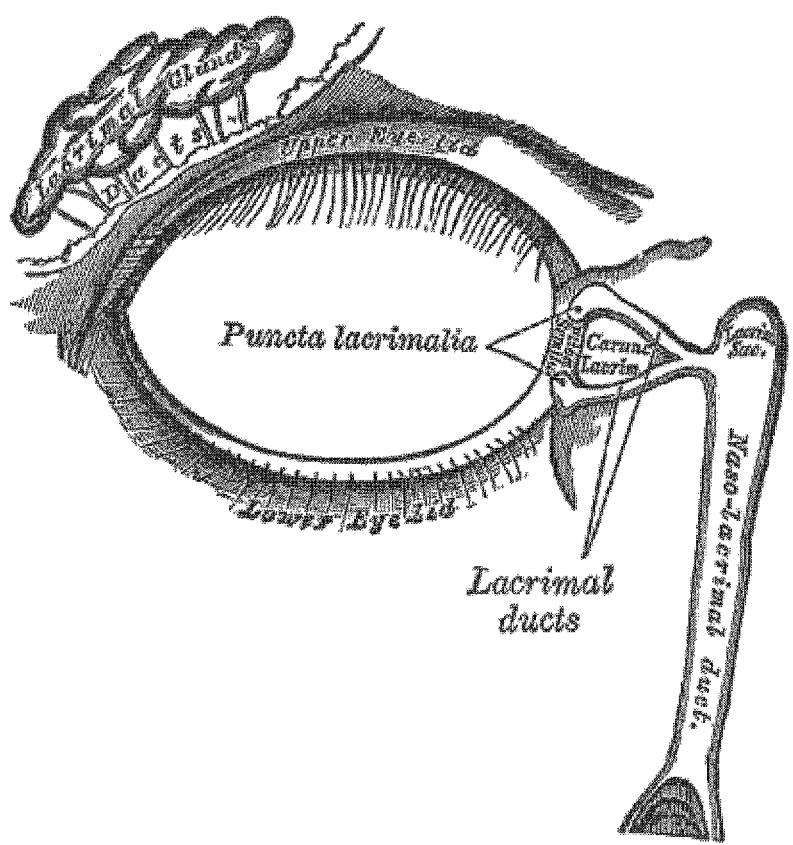
FIG. 4 shows a diagram of the lacrimal system. Herein, the upper and lower lacrimal ducts converge into the nasolacrimal duct. The device is envisioned to extend from the reservoir located in the lacrimal sac and extend from the reservoir via tube into either the upper or lower lacrimal duct terminating in a puncta lacrimalia (a punctum) with a flow limiting port 5.

One embodiment of the device design standing alone as shown in FIG. 2 and implanted in the lacrimal system as shown in FIG. 3. FIG. 2 and FIG. 3 shows an elastic reservoir 1 having a loading port and an exit port that can be filled and flushed and refilled . . . etc. This can be made of stretchy plastics or silicones. The therapeutic agent reside in both the reservoir 1 and the third tube 4 connected to said loading port prior to moving through the first tube 2 connected to said exit port and the second tube 3 comprising a flow limiting port 5 connected to said first tube 2. In one embodiment, said flow limiting port 5 is a faceplate containing flow limiting capabilities. In one embodiment, the first and second tube comprise one continuous tube connected to the exit port of the reservoir 1 terminating in said flow limiting port 5. In one embodiment, said flow limiting port 5 comprises a distal membrane 7. In one embodiment, as demonstrated in FIG. 3, the device comprises a second set of first 2 and second tubes 3 connected to the exit port of the reservoir 1 terminating in said flow limiting port 5. The third tube 4 is a connection to the nasal cavity through the nasolacrimal duct to allow for flushing of the elastic reservoir 1 or refilling of same. The terminal end of the third tube 4 can be clipped closed or pinched to be watertight. The second tube 3 is open to external punctum and tear film. A valve mechanism or small caliber opening will control flow of the fluid from this distal faceplate to the tear film; this is referred to as the flow limiting port 5. The rate of flow can be altered by modifying the elastic reservoir characteristics and/or the distal flow limiting mechanism at the faceplate. The first tube 2 is the canalicular (to be inserted in the lacrimal canal) portion of device contains lumen connecting the elastic reservoir 1 to the second tube 3 and to the tear film.

Figure 5:
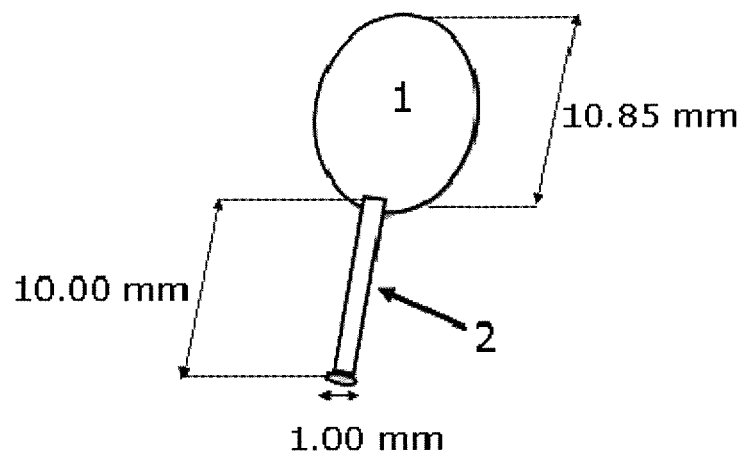
FIG. 5 shows an angled view of the device.
Figure 6:
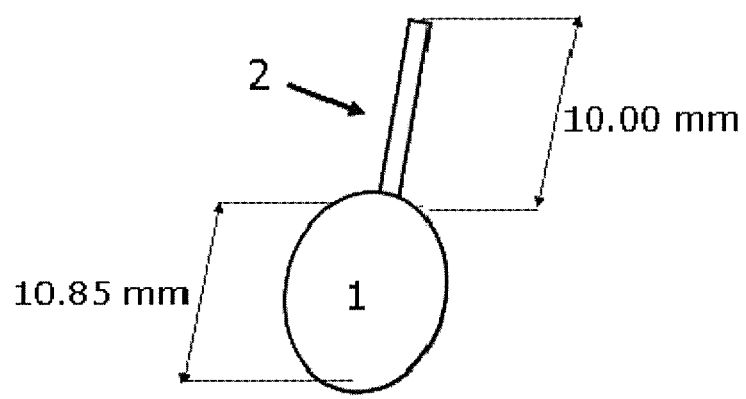
FIG. 6 shows an angled view of the device.
Figure 7:
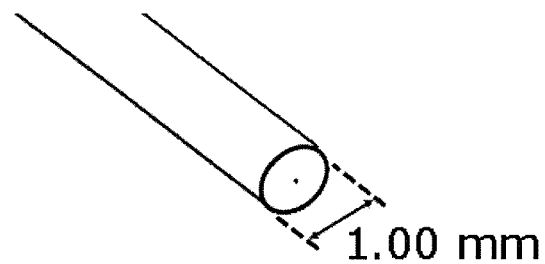
FIG. 7 shows a tube distal end close-up.
Figure 8A:
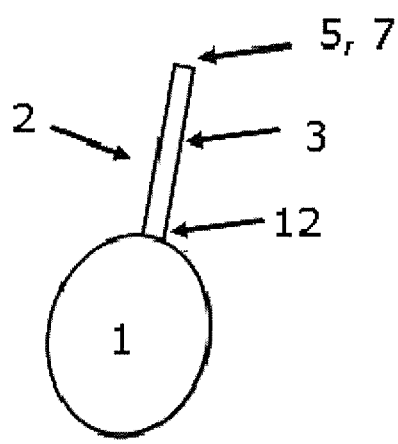
FIGS. 8A&B show one embodiment of the device.
Figure 8B:
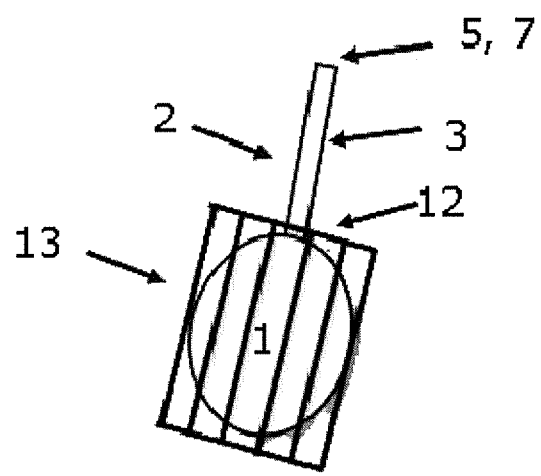
FIG. 8B shows that a nitinol cage 13 or other structural features may serve to exert pressure on the microporous balloon/reservoir 1.
Figure 9:
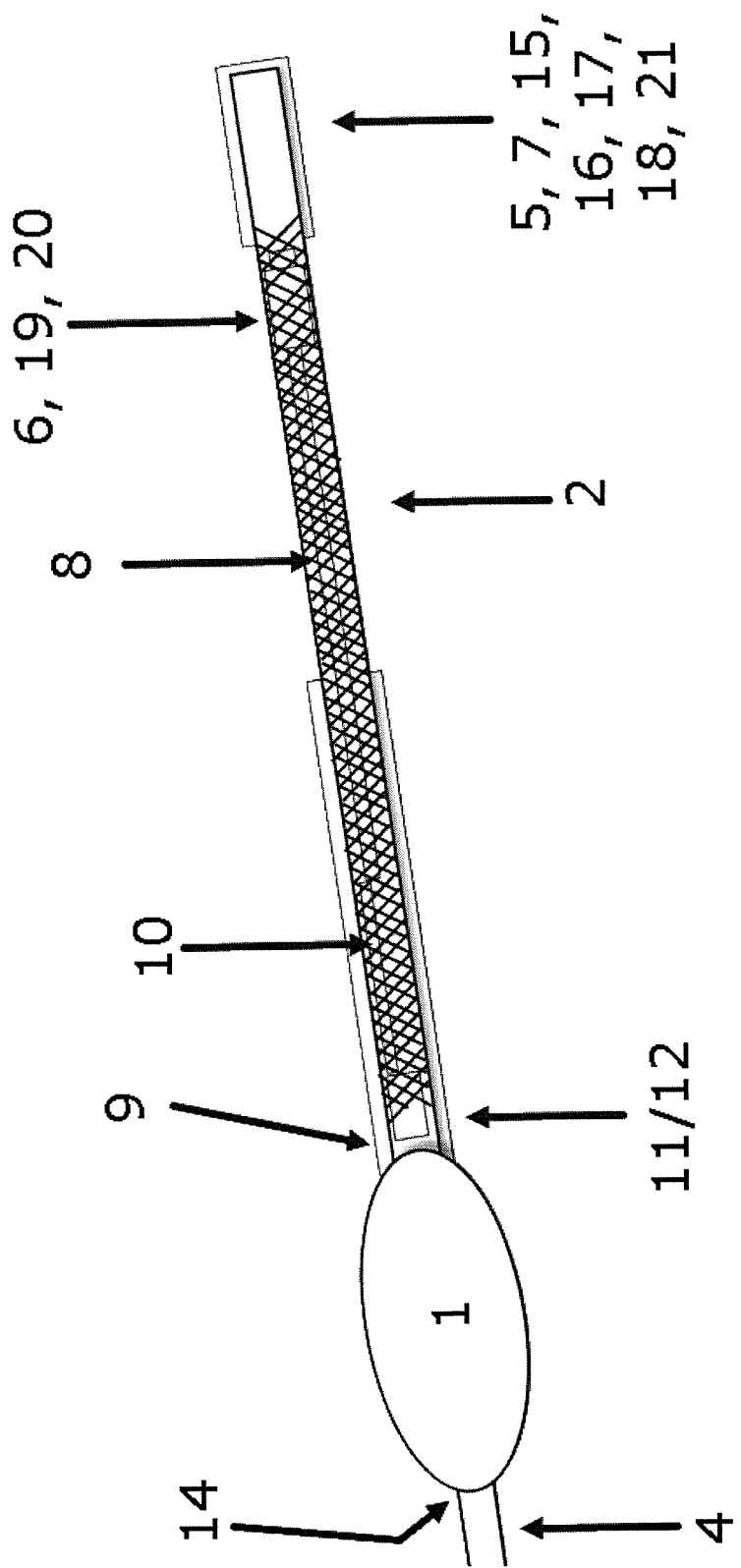
FIG. 9 shows a device where there is a miroporous balloon/elastic reservoir 1 and a distal membrane 7 where the first tube 2 contains bio erodible elements 6, and an internal plunger 8, and an exit port 9 is connected to internal springs 10 connected to said internal plunger 8, microelectromechanical systems spring pressure regulator 12, and bioerodible materials 6 open up inlet pores sequentially allowing along said internal composition column which would enable for pulsed dosing of the active agent composition.
Figure 10:
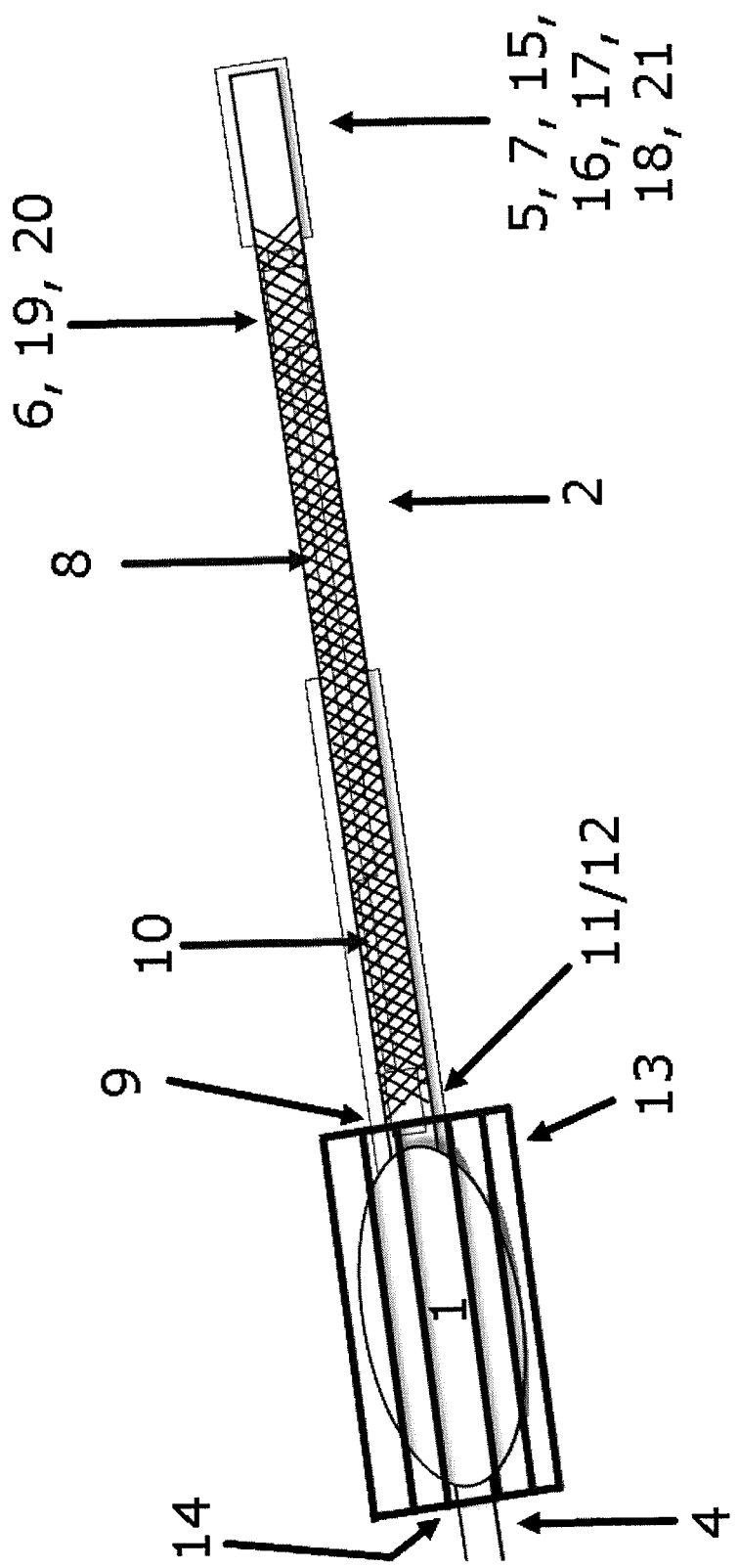
FIG. 10 shows one embodiment of the device where a separate nitinol device 13 is constructed to surround the reservoir 1 prior to filling so that the nitinol cage 13 contains straight wires. Once filled, the reservoir 1 pushes the nitinol out and the nitinol then acts on the non-elastic or semi-elastic material to slowly push fluid out towards the flow limiting membrane 7 at the top (exit port 9).

In one embodiment, the balloon component 1 of the device may be designed only for fixation and not delivery (like foley catheter retention feature). In one embodiment, nitinol wire (or other material) springs 10 are used internal to the lacrimal portion of the device that pulls an internal plunger 8 towards the distal opening as fluid is released to allow for constant fluid delivery without relying on a constant pressure elastomeric balloon 1. In one embodiment, the device comprises bioerodible or biodegradable materials 6. In one embodiment, said bioerodible 6 or biodegradable materials 6 open up inlet pores sequentially allowing along the internal fluid column which would enable for pulsed dosing. In one embodiment, the device further comprises a microelectromechanical systems (MEMS) spring pressure regulator 12. In one embodiment, ePTFE membranes 7 may be used to regulate flow out of the distal end of said device. In one embodiment, such a distal membrane 7 will control flow of the fluid from this distal faceplate to the tear film; this is referred to as the flow limiting port 5. For example, ePTFE with 0.0003"+/−0.0001" (0.00762 mm+/−0.00254 mm) thickness and with a porosity of 80%+/−10% and a mean flow pore size of 0.2 to 0.5 micron. In one embodiment, one or more layers of ePTFE material can be used for flow regulation. FIG. 5 shows shows an angled view of the device. FIG. 6 shows an angled view of the device. FIG. 7 shows a tube distal end close-up. FIGS. 8A&B show one embodiment of the device. FIG. 8A shows the device consisting of a microporous balloon 1 that can deliver drug directly to tissue spaces such as sinuses. In contains a tube (2, 3) with a flow limiting port/exit port 5 which may or may not contain a distal membrane 7 which can serve as a simple filling port 7 (located in the punctum or in the conjunctiva/caruncle or surrounding tissues) to refill the microporous balloon 1 as needed. The balloon 1 then oozes out medication/fluid to targeted tissues. FIG. 8B shows that a nitinol cage 13 or other structural features may serve to exert pressure on the microporous balloon/reservoir 1. Instead of drug/composition being delivered only through the distal membrane 7 or flow limiting port 5, this option provides the capability to deliver drug directly from the reservoir 1 to surrounding tissues with or without delivery through the distal part as well. There are certain diseases that would benefit from this approach, like chronic sinusitis. FIG. 9 shows a device where there is a miroporous balloon/elastic reservoir 1 and a distal membrane 7 where the first tube 2 contains bio erodible elements 6, and an internal plunger 8, and an exit port 9 is connected to internal springs 10 connected to said internal plunger 8, microelectromechanical systems spring pressure regulator 12, and bioerodible materials 6 open up inlet pores sequentially allowing along said internal composition column which would enable for pulsed dosing of the active agent composition. FIG. 10 shows one embodiment of the device where a separate nitinol device 13 is constructed to surround the reservoir 1 prior to filling so that the nitinol cage 13 contains straight wires. Once filled, the reservoir 1 pushes the nitinol out and the nitinol then acts on the non-elastic or semi-elastic material to slowly push fluid out towards the flow limiting membrane 7 at the top (exit port). In one embodiment, the elastic reservoir 1 will deliver fluid+/−active ingredients to the ocular surface at a fixed rate between 0.1 microliters and 30.0 microliters per day for a minimum of one week. In another embodiment, the delivery is achieved for a minimum of 60 days.

In one embodiment the device comprises a reservoir 1 and a first tube. In one embodiment, the device comprises a nonelastic reservoir 1 that is contained within surrounding material that allows for compression of said reservoir 1. In one embodiment, a nitinol wire, spring or cage 13 may be used to provide the compression of said reservoir 1. In one embodiment, the reservoir 1 is substantially nonelastic. In one embodiment, said reservoir 1 is made from a microporous or naonoporous material. In one embodiment, the composition within said reservoir 1 is released through the pores of the reservoir material. In some embodiments, the device comprises a protective sleeve be placed over said reservoir. In one embodiment, said sleeve protects against leaks entering the nasal duct or other tissue compartments. In one embodiment, said device contains fluorescent material or coloring to allow for detection and postion confirmation by the user (physician or patient). In one embodiment, said reservoir is implanted within the sinuses surrounding the eye. In one embodiment, the punctal portion or distal end allows for filling the elastic reservoir with medication, but the elastic reservoir 1 sits in a sinus and allows for delivery of drug through a microporous balloon. In one embodiment, the punctal portion is implanted through the caruncle or through the conjunctiva (similar to implantation of a jones tube) and allow for the microporous balloon pump to deliver drug directly to the sinus or other tissue areas surrounding the eye. In another embodiment, the device delivers medication through a microporous reservoir in addition to the primary embodiment that delivers to a tube with a hole positioned at the punctum.

As discussed above, the present invention provides compositions, methods and devices relating to a lacrimal, eye, sinuses and/or periocular tissues system implant devices, which greatly increase their ability to deliver therapeutic agents consistently with a simple straightforward design and in larger quantities than is currently available. In one aspect, the present invention provides for the combination of various therapeutic agents and lacrimal, eye, sinuses and/or periocular tissues system implant for use in medical intervention, continuing medical therapy, and/or cosmetic or reconstructive surgery. In one aspect, the present invention is a lacrimal, eye, sinuses and/or periocular tissues system therapeutic agent delivery device for use in medical intervention, continuing medical therapy, and/or cosmetic or reconstructive surgery.

In some examples, an antimicrobial coating can be disposed on, or impregnated in, at least a portion of the outer surface of the implant body to further prevent microbial growth on the implant body. In an example, the antimicrobial coating can include an agent selected from the group comprising 2-bromo-2-nitropropane-1,3-diol, 5-bromo-5-nitro-1,3-dioxane, 7-ethyl bicyclooxazolidine, benzalkonium chloride, benzethonium chloride, benzoic acid, benzyl alcohol, boric acid, bronopol, cetylpyridinium chloride, chlorhexidine digluconate, chloroacetamide, chlorobutanol, chloromethyl isothiazolinone and methyl isothiazoline, dimethoxane, dimethyl oxazolidine, dimethyl hydroxymethyl pyrazole, chloroxylenol, dehydroacetic acid, diazolidinyl urea, dichlorobenzyl alcohol, DMDM hydantoin, ethyl alcohol, fottnaldehyde, glutaraldehyde, hexachlorophene, hexetidine, hexamethylenetramine, imidazolidinyl urea, iodopropynyl butylcarbamate, isothiazolinones, methenammonium chloride, methyldibromo glutaronitrile, MDM hydantoin, minocycline, ortho phenylphenol, p-chloro-m-cresol, parabens (butylparaben, ethylparaben, methylparaben), phenethyl alcohol, phenoxyethanol, piroctane olamine, polyaminopropyl biguanide, polymethoxy bicyclic oxazolidine, polyoxymethylene, polyquaternium-42, potassium benzoate, potassium sorbate, propionic acid, quaternium-15, rifampin, salicylic acid, selenium disulfide, sodium borate, sodium iodate, sodium hydroxymethylglycinate, sodium propionate, sodium pyrithione, sorbic acid, thimerosal, triclosan, triclocarban, undecylenic acid, zinc phenosulfonate, and zinc pyrithione. In an example, the antimicrobial coating can include a material selected from the group comprising silver lactate, silver phosphate, silver citrate, silver acetate, silver benzoate, silver chloride, silver iodide, silver iodate, silver nitrate, silver sulfadiazine, silver palmitate or one or more mixtures thereof. In an example, the antimicrobial coating can include at least one of an antibiotic or an antiseptic. For instance, the antimicrobial coating can include a temporary anesthetic lasting, on average, between a few hours and a day. In still other examples, the antimicrobial coating can include a drug use to treat an underlying disease, such as a bolus for immediate effect.

A therapeutic agent (or simply "agent") can comprise, among other things, a drug made from one or any combination of the following or their equivalents, derivatives or analogs, including, anti-glaucoma medications, (e.g. adrenergic agonists, adrenergic antagonists (beta blockers), carbonic anhydrase inhibitors (CAIS, systemic and topical), parasympathomimetics, prostaglandins and hypotensive lipids, and combinations thereof), antimicrobial agent (e.g., antibiotic, antiviral, antiparacytic, antifungal, etc.), a corticosteroid or other anti-inflammatory (e.g., an NSAID or other analgesic and pain management compounds), a decongestant (e.g., vasoconstrictor), an agent that prevents of modifies an allergic response (e.g., an antihistamine, cytokine inhibitor, leucotriene inhibitor, IgE inhibitor, immunomodulator), a mast cell stabilizer, cycloplegic, mydriatic or the like.

Example available agents include, but are not limited to, thrombin inhibitors; antithrombogenic agents; thrombolytic agents; fibrinolytic agents; vasospasm inhibitors; vasodilators; antihypertensive agents; antimicrobial agents, such as antibiotics (such as tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate), antifungals (such as amphotericin B and miconazole), and antivirals (such as idoxuridine trifluorothymidine, acyclovir, gancyclovir, interferon); inhibitors of surface glycoprotein receptors; antiplatelet agents; antimitotics; microtubule inhibitors; anti-secretory agents; active inhibitors; remodeling inhibitors; antisense nucleotides; anti-metabolites; antiproliferatives (including antiangiogenesis agents); anticancer chemotherapeutic agents; anti-inflammatories (such as hydrocortisone, hydrocortisone acetate, dexamethasone 21-phosphate, fluocinolone, medrysone, methylprednisolone, prednisolone 21-phosphate, prednisolone acetate, fluorometyhalone, betamethasone, triamcinolone, triamcinolone acetonide); non steroidal anti-inflammatories (NSAIDs) (such as salicylate, indomethacin, ibuprofen, diclofenac, flurbiprofen, piroxicam indomethacin, ibuprofen, naxopren, piroxicam and nabumetone). Examples of such anti-inflammatory steroids contemplated for use with the present lacrimal implants, include triamcinolone acetonide (generic name) and corticosteroids that include, for example, triamcinolone, dexamethasone, fluocinolone, cortisone, prednisolone, flumetholone, and derivatives thereof.); antiallergenics (such as sodium chromoglycate, antazoline, methapyriline, chlorpheniramine, cetrizine, pyrilamine, prophenpyridamine); anti proliferative agents (such as 1,3-cis retinoic acid, 5-fluorouracil, taxol, rapamycin, mitomycin C and cisplatin); decongestants (such as phenylephrine, naphazoline, tetrahydrazoline); miotics and anti-cholinesterase (such as pilocarpine, salicylate, carbachol, acetylcholine chloride, physostigmine, eserine, diisopropyl fluorophosphate, phospholine iodine, demecarium bromide); antineoplastics (such as carmustine, cisplatin, fluorouracil; immunological drugs (such as vaccines and immune stimulants); hormonal agents (such as estrogens,—estradiol, progestational, progesterone, insulin, calcitonin, parathyroid hormone, peptide and vasopressin hypothalamus releasing factor); immunosuppressive agents, growth hormone antagonists, growth factors (such as epidermal growth factor, fibroblast growth factor, platelet derived growth factor, transforming growth factor beta, somatotrapin, fibronectin); inhibitors of angiogenesis (such as angiostatin, anecortave acetate, thrombospondin, anti-VEGF antibody); dopamine agonists; radiotherapeutic agents; peptides; proteins; enzymes; extracellular matrix; components; ACE inhibitors; free radical scavengers; chelators; antioxidants; anti polymerases; photodynamic therapy agents; gene therapy agents; and other therapeutic agents such as prostaglandins, antiprostaglandins, prostaglandin precursors, including antiglaucoma drugs including beta-blockers such as Timolol, betaxolol, levobunolol, atenolol, and prostaglandin analogues such as bimatoprost, travoprost, latanoprost etc; carbonic anhydrase inhibitors such as acetazolamide, dorzolamide, brinzolamide, methazolamide, dichlorphenamide, diamox; and neuroprotectants such as lubezole, nimodipine and related compounds; and parasympathomimetrics such as pilocarpine, carbachol, physostigmine and the like.

Additional agents that can be used with the present lacrimal implants include, but are not limited to, drugs that have been approved under Section 505 of the United States Federal Food, Drug, and Cosmetic Act or under the Public Health Service Act. The present lacrimal implants can also be used with drugs listed in the FDA Orange Book that has or records the same date as, earlier date than, or later date than, the filing date of this patent document. For example, these drugs can include but are not limited to, among others, dorzolamide, olopatadine, travoprost, bimatoprost, cyclosporin, brimonidine, moxifloxacin, tobramycin, brinzolamide, aciclovir timolol maleate, ketorolac tromethamine, prednisolone acetate, sodium hyaluronate, nepafenac, bromfenac, diclofenac, flurbiprofen, suprofenac, binoxan, patanol, dexamethasone/tobramycin combination, moxifloxacin, or acyclovir.

Examples of diseases or disorders that can be treated with above-listed agents include, but are not limited to, glaucoma, pre- and post-surgical ocular treatments, dry eye, anti-eye allergy, anti-infective, post-surgical inflammation or pain, or respiration-related disorders, such as allergies In some examples, the therapeutic agent can include a lubricant or a surfactant, for example a lubricant to treat dry eye. In other examples, the therapeutic agent can include an absorbent capable of absorbing tear from an eye.

Although the form of the therapeutic agent is envisioned to be a liquid with a flow limited release through a port connected to the reservoir, is also possible that the drug supply can comprise one or more biocompatible materials capable of providing a sustained release of the one or more agents. For example, a biodegradable matrix, a porous drug supply, or liquid drugs supply. A matrix that includes the agents can be formed from either biodegradable or non-biodegradable polymers. In some examples, a non-biodegradable drug supply can include, but are not limited to, silicone, acrylates, polyethylenes, polyurethane, polyurethane, hydrogel, polyester (e.g., DACRON® from E. I. Du Pont de Nemours and Company, Wilmington, Del.), polypropylene, polytetrafluoroethylene (PTFE), expanded PTFE (ePTFE), polyether ether ketone (PEEK), nylon, extruded collagen, polymer foam, silicone rubber, polyethylene terephthalate, ultra high molecular weight polyethylene, polycarbonate urethane, polyurethane, polyimides, stainless steel, nickel-titanium alloy (e.g., Nitinol), titanium, stainless steel, cobalt-chrome alloy (e.g., ELGILOY® from Elgin Specialty Metals, Elgin, Ill.; CONICHROME® from Carpenter Metals Corp., Wyomissing, Pa.). In some examples, a biodegradable drug supply can comprise one or more biodegradable polymers, such as protein, hydrogel, polyglycolic acid (PGA), polylactic acid (PLA), poly(L-lactic acid) (PLLA), poly(L-glycolic acid) (PLGA), polyglycolide, poly-L-lactide, poly-D-lactide, poly(amino acids), polydioxanone, polycaprolactone, polygluconate, polylactic acid-polyethylene oxide copolymers, modified cellulose, collagen, polyorthoesters, polyhydroxybutyrate, polyanhydride, polyphosphoester, poly(alpha-hydroxy acid) and combinations thereof. In some examples, the drug supply can comprise a hydrogel polymer. Any drug supply matrix must be capable of compression controlled release through the previously described port.

EXAMPLES

The following examples are provided in order to demonstrate and further illustrate certain preferred embodiments and aspects of the present invention and are not to be construed as limiting the scope thereof.

Example 1

One Embodiment, Supporting Data

Given the numerous fluid properties of artificial tears and other topical medications and the elasticity components of the potential materials to be used, sample calculations have been done to create a logical starting ground for experimentation. Below is summary of the calculations performed for each of the 3 sample types (PTFE, Silicon Rubber, Polyimide). Using a spreadsheet, the Benoulli's flow equation, as well as the elastic properties of the balloon material such as Young's modulus and diameter of distal end, the following estimations have been calculated to give a 7 microlitre/day flow rate and allow the balloon to function for 100 days:
PTFE:
Inner Tube Diameter: $1.56 \times 10^{-6}$ m
Elastic Reservoir Volume: $7 \times 10^{-4}$ L
Polyimide:
Inner Tube Diameter: $8.43 \times 10^{-7}$ m
Elastic Reservoir Volume: $7 \times 10^{-4}$ L
Silicone Rubber:
Inner Tube Diameter: $3.37 \times 10^{-6}$ m
Elastic Reservoir Volume: $7 \times 10^{-4}$ L These calculations were made by first assuming an inner tube diameter and starting elastic reservoir volume. The surface area of the inflated balloon corresponding to the elastic reservoir volume was calculated and thus the radius of the balloon was known. Given the surface area of the balloon, Young's modulus was used to calculate a pressure exerted by the balloon on the fluid and thus a net pressure was calculated inside the balloon. Given this pressure, the density of the fluid, and the Bernoulli's assumptions of free jet at the distal end point as well as negligible fluid velocity at the balloon center, the unknown velocity variable at the end of the device was calculated. The inner tube diameter was then iteratively adjusted to correspond to a 7 microlitre per day flow rate and further adjusted to match the 100 day life criteria. Using the design shown in FIG. 5, FIG. 6, and FIG. 7, 7 microliters of fluid was consistently delivered over a period no less than 90 days.

Thus, specific compositions and methods of lacrimal system drug delivery device have been disclosed. It should be apparent, however, to those skilled in the art that many more modifications besides those already described are possible without departing from the inventive concepts herein. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

REFERENCES

1. Fleisher, D. et al. (1996) "Improved oral drug delivery: solubility limitations overcome by the use of prodrugs," *Adv. Drug Delivery Rev.* 19(2), 115-130.
2. Smith, C. D. et al. (1994) "A sensitive assay for taxol and other microtubule-stabilizing agents," *Cancer Lett.* 79(2), 213-219.
3. Mooberry, S. L. et al. (1995) "Tubercidin stabilizes microtubules against vinblastine-induced depolymerization, a taxol-like effect," *Cancer Lett.* 96(2), 261-266.
4. Ro, A. J. et al. (2012) "Morphological and degradation studies of sirolimus-containing poly(lactide-co-glycolide) discs," *Journal of Biomedical Materials Research Part B: Applied Biomaterials* 100B(3), 767-777.
5. Sim, S. et al. "Composite Lacrimal Insert and Related Methods," United States Patent Application Publication Number 20100034870, application Ser. No. 12/432,553, filed Apr. 29, 2009. (published Feb. 11, 2010).
6. Hubbell, J. A. et al. "Photopolymerizable biodegradable hydrogels as tissue contacting materials and controlled-release carriers," U.S. Pat. No. 5,410,016, application Ser. No. 08/022,687, filed Mar. 1, 1993. (issued Apr. 25, 1995).
7. Rodstrom, T. R. et al. "Punctal Plugs and Methods of Delivering Therapeutic Agents," United States Patent Application Publication Number 20080181930, application Ser. No. 12/022,520, filed Jan. 30, 2008. (published Jul. 31, 2008).
8. Borgia, M. J. et al. "Punctal Plugs for the Delivery of Active Agents," United States Patent Application Publication Number 20070298075, application Ser. No. 11/759,327, filed Jun. 7, 2007. (published Dec. 27, 2007).
9. Beeley, N. R. F. and Coldren, B. A. "Punctal Plugs for Controlled Release of Therapeutic Agents," United States Patent Application Publication Number 20110251568, application Ser. No. 13/043,171, filed Mar. 8, 2011. (published Oct. 13, 2011).
10. Brubaker, M. J. et al. "Sustained Release Drug Delivery Devices," WIPO PCT Patent Publication Number WO/2002/056863, Application PCT/US2001/048804, filed Jul. 25, 2002. (published Dec. 17, 2001).
11. Rapacki, A. R. et al. "Lacrimal Implants and Related Methods," United States Patent Application Publication Number 20100274204, application Ser. No. 12/710,855, filed Feb. 23, 2010. (published Oct. 28, 2010).
12. Cohan, B. E. "Opthalmic insert and method for sustained release of medication to the eye," European Patent EP1891942B1, Application EP1178779A1, filed Apr. 7, 2000. (issued Mar. 3, 2010).
13. Murube, J. et al. (2003) "Subcutaneous abdominal artificial tears pump-reservoir for severe dry eyes," *Orbit* 22(1), 29.

I claim:

1. A lacrimal system drug delivery device, comprising:
   a) a self-compressible reservoir at a distal end of said lacrimal system drug delivery device to receive a fluid, fill to distortion, and provide a force to deliver said fluid at a fixed rate between 0.1 microliters and 30.0 microliters per day for a minimum of one week, said self-compressible reservoir having a reservoir port for loading and delivering said fluid, and said self-compressible reservoir having elastic properties to compress said fluid inside said self-compressible reservoir responsive to said distortion;
   b) a first lumen connected to said reservoir port, to load said fluid into said self-compressible reservoir; and
   c) a second lumen to deliver said fluid from said self-compressible reservoir, wherein the first lumen is not comprised within the second lumen, wherein said second lumen terminates with a flow limiting port in at least one punctum in contact with a tear film of an eye, said flow limiting port located at a proximal end of said lacrimal system drug delivery device.

2. The device of claim 1, wherein said fluid comprises a composition with an active ingredient.
3. The device of claim 1, wherein said self-compressible reservoir enables anatomical fixation.
4. The device of claim 3, wherein said anatomical fixation is a device retention feature.
5. The device of claim 1, wherein said reservoir port is connected to an internal plunger.
6. The device of claim 5, wherein said reservoir port is connected to internal springs connected to said internal plunger.
7. The device of claim 6, wherein said device further comprises a microelectromechanical systems spring pressure regulator.
8. The device of claim 1, wherein said device is made of bioerodible materials.
9. The device of claim 1, wherein said device is made of microporous materials.
10. The device of claim 1, wherein said device is made of nanoporous materials.
11. The device of claim 1, wherein said device is made of medical grade materials.
12. The device of claim 1, wherein said flow limiting port comprises at least one hole.
13. The device of claim 1, wherein said flow limiting port comprises a filter.
14. The device of claim 1, wherein said flow limiting port comprises at least one ePTFE membrane.
15. The device of claim 1, wherein a flow of said fluid out of said device is additionally gravity dependent.
16. The device of claim 15, wherein the flow of said fluid out of said device is limited by a gravity dependent valve.
17. A method of treatment of a subject comprising a lacrimal system comprising at least one lacrimal duct, at least one punctum, a lacrimal sac and a nasolacrimal duct, the method comprising:
   a) providing:
      i) a lacrimal system drug delivery device, comprising:
         A) a self-compressible, elastic reservoir at a distal end of said lacrimal system drug delivery device capable of insertion inside said lacrimal sac, said self-compressible, elastic reservoir to receive a fluid, fill to distortion, and provide a force to deliver said fluid at a fixed rate between 0.1 microliters and 30.0 microliters per day for a minimum of one week,
         B) a first lumen to deliver said fluid into said self-compressible, elastic reservoir; and
         C) a second lumen to deliver said fluid from said self-compressible, elastic reservoir, wherein the first lumen is not comprised within the second lumen, said second lumen terminating with a flow limiting port in said at least one punctum in contact with a tear film of an eye, said flow limiting port at a proximal end of said lacrimal system drug delivery device,
   b) inserting said drug delivery device into said lacrimal system;

c) providing said fluid comprising a composition with at least one active ingredient to said self-compressible, elastic reservoir, and d) administering said composition to said subject using said lacrimal system drug delivery device.

18. The method of claim 17, wherein said device further comprises at least one internal spring connected to an internal plunger connected to a reservoir port.

19. The method of claim 18, wherein said internal plunger enables a constant release of said composition without relying on said elastic reservoir.

20. The method of claim 18, wherein said device further comprises a microelectromechanical systems spring pressure regulator.

21. The method of claim 17, wherein said device further comprises a cut-off valve.

22. The method of claim 21, wherein a flow out of said device is controlled by said cut-off valve that is accessible by an operator to decrease said flow at given times when treatment is not desired.

23. The method of claim 17, wherein said device comprises bioerodible materials.

24. The method of claim 23, wherein said device comprises internal composition columns with said bioerodible materials.

25. The method of claim 24, wherein an erosion of said bioerodible materials opens up inlet pores to said internal composition columns to enable pulsed dosing of said composition.

26. The method of claim 17, wherein said at least one active ingredient is selected from the group consisting of artificial tears, glaucoma drops, anti-inflammatory agents, nonsteroidal agents, antibiotics, biologics, proteins, aptamers, nucleic acids, cytokines, plasma, sympathomimetics, parasympathomimetics, prostaglandin analogues, beta blockers, alpha-agonists, and anti-VEGF agents.

27. The method of claim 17, wherein said flow limiting port regulates a flow of said composition from said device.

28. The method of claim 17, wherein said flow limiting port comprises at least one ePTFE membrane.

29. The method of claim 17, wherein said flow limiting port comprises at least one layer of ePTFE material.

\* \* \* \* \*